United States Patent

Beutel et al.

[11] Patent Number: 5,976,813
[45] Date of Patent: *Nov. 2, 1999

[54] CONTINUOUS FORMAT HIGH THROUGHPUT SCREENING

[75] Inventors: Bruce A. Beutel, Libertyville; Mark E. Schurdak, Antioch; Martin J. Voorbach, Vernon Hills; David J. Burns, Round Lake Park; Mary K. Joseph, Libertyville, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/990,168
[22] Filed: Dec. 12, 1997
[51] Int. Cl.[6] .................................................. G01N 33/53
[52] U.S. Cl. ...................... 435/7.1; 435/7.92; 435/7.93; 436/170; 436/518; 436/535; 422/56
[58] Field of Search ..................................... 435/7.1, 7.92, 435/7.93, 7.94, 7.9, 975; 436/170, 518, 531, 535, 810; 422/56

[56] References Cited

U.S. PATENT DOCUMENTS 4,447,526  5/1984  Rupchock et al. .
4,591,570  5/1986  Chang ........................................ 436/518
5,711,915  1/1998  Siegmund et al. .

FOREIGN PATENT DOCUMENTS 2 291 708  1/1996  United Kingdom .

OTHER PUBLICATIONS

The First Annual Conference of The Society for Biomolecular Screening: 17–25 (Nov. 7, 1995).
Comley et al., *Journal of Biomolecular Screening*, 2 (3): 171–178 (1997).
Salmon et al., *Molecular Diversity*, 2: 57–63 (1996).
Jayawickreme et al., *Proc. Natl. Acad. Sci. USA*, 91: 1614–1618 (1994).
Hutchins, "A New Western Blotting Variant", *Bio Techniques*, vol. 7, No. 3(1989), pp. 248–250(?).

Primary Examiner—Jeffrey Stucker
Attorney, Agent, or Firm—Janelle D. Strode; Lawrence S. Pope

[57] ABSTRACT

Continuous format high throughput screening (CF-HTS) using at least one porous matrix allows the pharmaceutical industry to simultaneously screen large numbers of chemical entities for a wide range of biological or biochemical activity. In addition, CF-HTS is useful to perform multi-step assays.

14 Claims, 19 Drawing Sheets

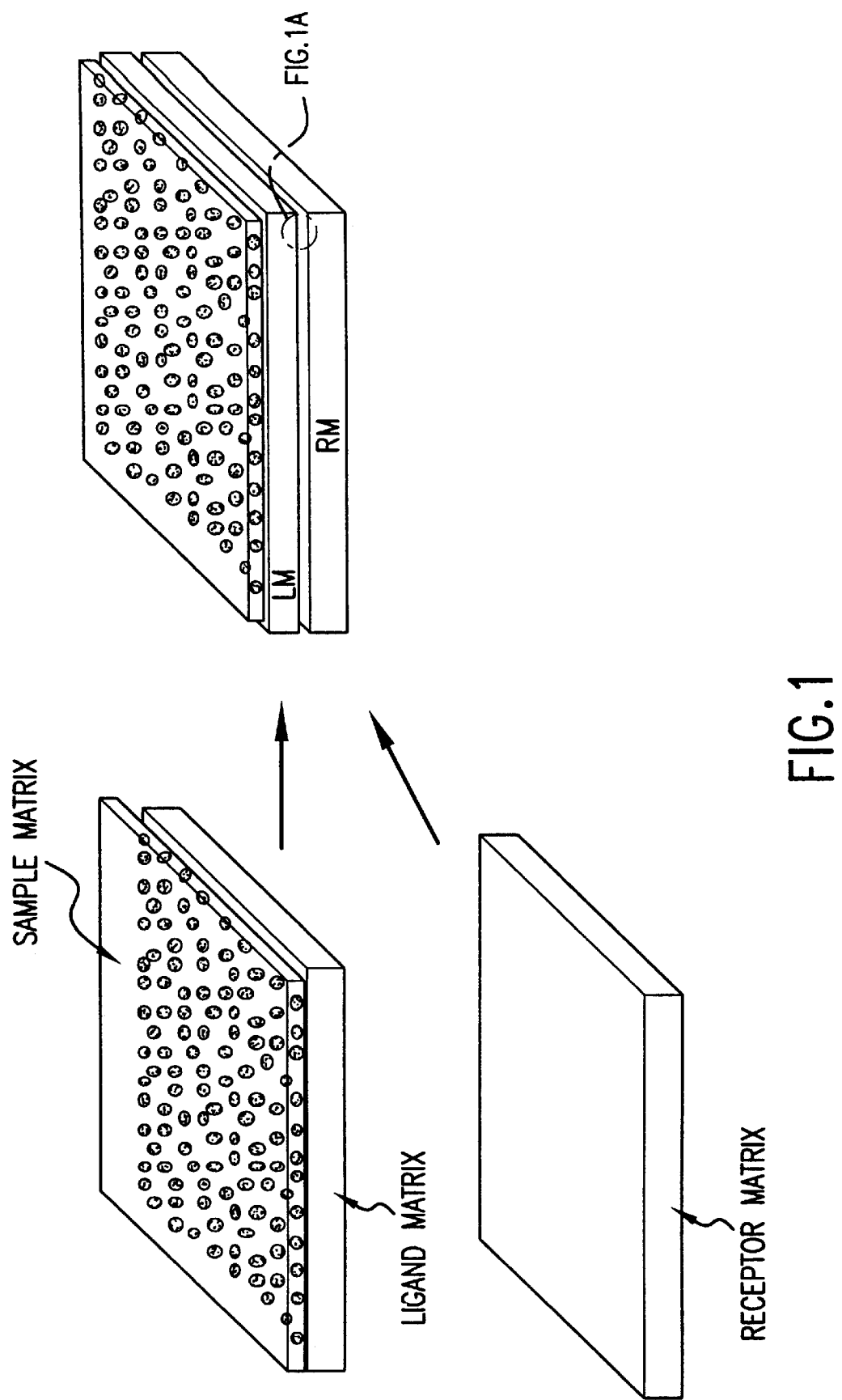

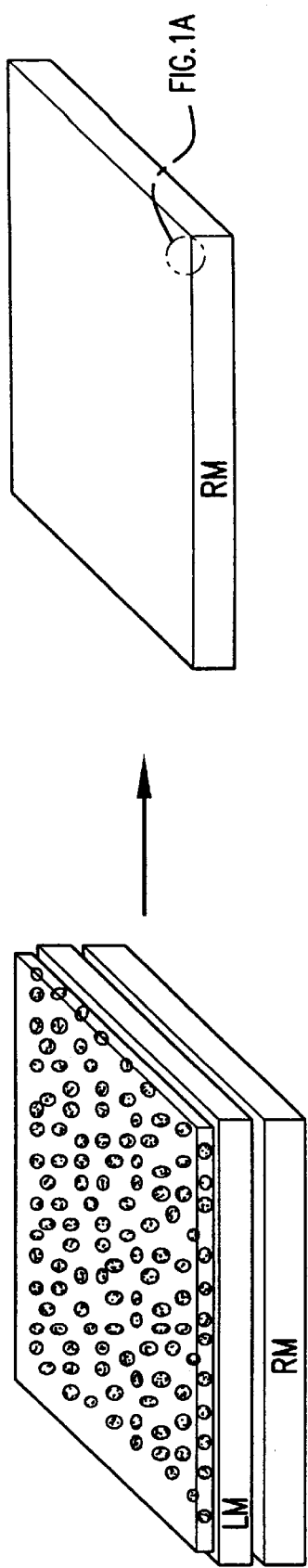
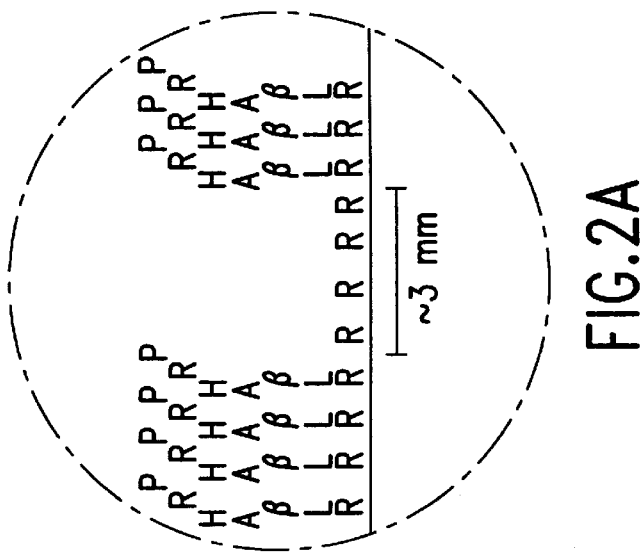
FIG. 2
FIG. 2A

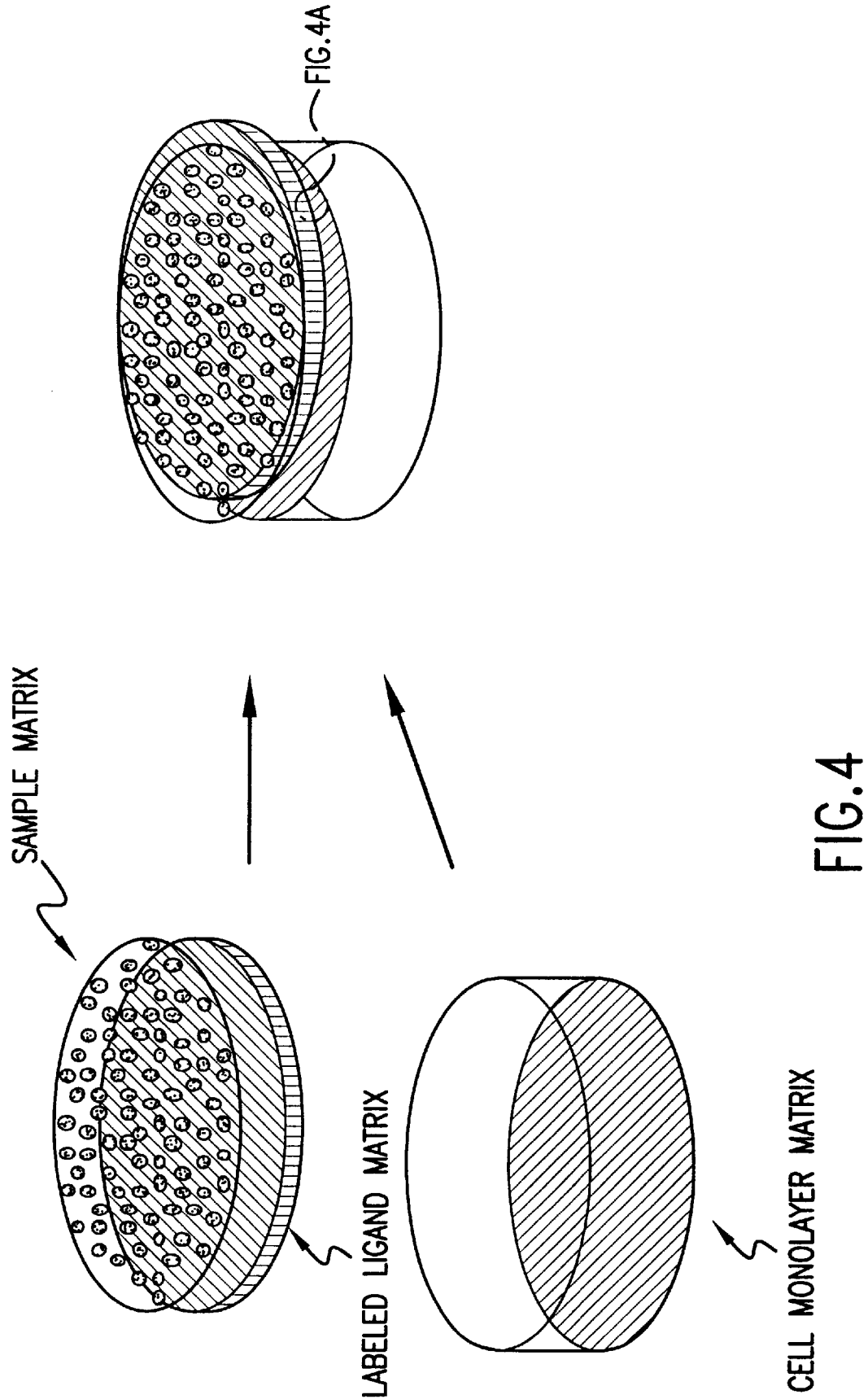

CONTINUOUS FORMAT HIGH THROUGHPUT SCREENING

TECHNICAL FIELD OF THE INVENTION

Continuous format high throughput screening (CF-HTS) using at least one porous matrix allows the pharmaceutical industry to simultaneously screen large numbers of chemical entities for a wide range biological or biochemical activity. In addition, CF-HTS is useful to perform multi-step assays.

BACKGROUND OF THE INVENTION

Biochemical and biological assays are designed to test for activity in a broad range of systems ranging from protein-protein interactions, enzyme catalysis, small molecule-protein binding, to cellular functions. In "High Throughput Screening" (HTS), one uses these kinds of assays to test a large number of chemical entities in order to discover previously unknown biological or biochemical activities of the chemical entities.

Homogeneous vs. Heterogeneous Assays

All of the different kinds of biological assays can be divided into two major classes: homogeneous assays and heterogeneous assays. In homogeneous assays, all reagents are added together and the results are measured or interpreted without any additional manipulation. For example, cells grown on a petri dish can be exposed to a chemical. If the chemical is toxic to the cells, a clearing zone will indicate toxicity by simple observation. For another example, one can use cells that express a protein which changes the cell's color. In the case of beta-galactosidase ($\beta$-gal) expressing cells growing in agar containing x-gal, the cells become more or less blue depending how much of the $\beta$-gal protein is expressed. Thus, one can construct a homogeneous assay for any biological step that affects the expression of a reporter gene such as the beta-galactosidase gene. Yet another example of a homogeneous assay utilizes a substrate that changes color or fluorescence when it is processed by an enzyme. Finally, technologies such as Scintillation Proximity Assays (SPA) by Amersham directly measure binding of a radiolabeled ligand to a protein or any ligand binding substance fixed to beads that contain scintillant. All of the foregoing examples are homogeneous assays because they require no steps other than the addition of reagents prior to the final detection, measurement, or reading of the signal.

Heterogeneous assays, on the other hand, require at least two steps that, because they are inherently incompatible to some degree, cannot be combined into one step. For example, many heterogeneous assays require adding the reagents in a certain order (e.g., when some reagents would interfere with early steps of the assay but are required to complete later steps). Common examples of this include assays in which signal development reagents are added to indirectly report on the presence or concentration of a reaction product. Another common step in heterogeneous assays is a washing step. Excess assay reagents must often be added early in an assay, but need to be washed away before subsequent steps so that reactions can proceed without high background signal. For example, in a radioligand binding assay, a labeled ligand is first incubated with a protein that is bound to a solid surface, but only a small fraction of the ligand actually binds to the limited number of protein sites. After incubation, the excess of unbound ligand must be washed away before an accurate measurement can be made of the bound radioactive ligand. Washing can be achieved by a variety of alternative methods, including filtration, cycles of wash/decant, precipition/phase separation, and/or centrifugation.

Many biological and biochemical processes can be measured by heterogeneous methods only. Further, despite the existence of ways to adapt other biological and biochemical processes to homogeneous methods, these other processes work more cost effectively and/or with more readily available reagents by heterogeneous methods. A variety of methods and kits for homogeneous techniques such as SPA (Amersham), Fluorescence Polarization (Jolley and others), and Time Resolved Fluorescence (Packard and others) to name just a few are commercially available. However, using these kinds of methods always incurs additional cost and time. For many assays, the heterogeneous methods are more established and are easier to develop quickly. For this reason, use of heterogeneous methods such as ELISA, filter binding, RIA, Luciferase cell assays, etc. continue to be widespread. Some these methods will be described in greater detail below.

High Throughput Screening (HTS)

Through the years, the pharmaceutical industry has increasingly relied on HTS of libraries of chemical compounds to find drug candidates. HTS describes a method where many discrete compounds are tested in parallel so that large numbers of test compounds are screened for biological activity simultaneously or nearly simultaneously. Currently, the most widely established techniques utilize 96-well microtitre plates. In this format, 96 independent tests are performed simultaneously on a single 8 cm×12 cm plastic plate that contains 96 reaction wells. These wells typically require assay volumes that range from 50 to 500 $\mu$l. In addition to the plates, many instruments, materials, pipettors, robotics, plate washers and plate readers are commercially available to fit the 96-well format to a wide range of homogeneous and heterogeneous assays.

To date, efforts to improve HTS have focused on making the wells smaller (miniaturization). As one reduces the well size, one can increase the number of wells on each plate to provide more parallel testing. Further, by decreasing the assay volumes, one also decreases the cost of reagents per test. Moreover, because one can run more parallel tests with smaller assay volumes, one can also simultaneously test more compounds to find drug candidates. So far, miniaturization has marginally improved the 96-well technology by providing a 384-well (96×4) format. See Comley et al., *J. Biomol. Screening*, vol. 2(3), pp. 171–78 (1997). In fact, even higher density formats have been reported, including a 9600-well format. However, miniaturization has inherent costs and complexities.

These costs and complexities relate directly with the three primary components of miniaturizing a screening format. First, one must be able to make the test containers (tubes, wells, dimples, etc.) smaller. Second, one must be able to accurately dispense all of the necessary assay reagents into more and smaller wells (usually accomplished by liquid handling robots that simultaneously dispense the reagents into many wells). Third, one must be able to "read" the results of the tests in the high density array.

Given the requirements of parallelized independent assays, each component provides challenges and limits to how much miniaturization is feasible or cost effective. For example, a newer, smaller format may require a completely different method of dispensing reagents, or require a reading instrument that has the resolution, sensitivity and engineering that is compatible with the newer, miniaturized format. As one reduces the size of each well, one's ability to fabricate the container array, to dispense reagents in smaller quantities, and to read each test sample also becomes more difficult, time consuming, and costly. Further, a smaller sample size also increases the statistical variability from sample to sample because of the inherent inaccuracies in dispensing smaller volumes of reagents and in measuring weaker sample signals. Moreover, as sample size decreases beyond a certain point, factors like evaporation and surface tension add even greater cost and complexity to implementing the newer, miniaturized formats.

For a quantum leap in HTS technology, the industry wistfully yearns for the possibility of "free format assays" or assays that have no physical barrier between samples. Typically envisioned as testing small droplets in a format devoid of any wells, nobody has actually reported the use of a free-format assay in HTS with standard discrete-compound collections.

Screening Combinatorial Libraries—Gel Permeation Methods

With the advent of combinatorial chemistry, millions of chemical entities can be rapidly produced on solid supports (generally beads). Although the 96-well format is being used to screen bead-based libraries, this format is generally regarded as ineffective because (1) each bead carries only a small quantities of a chemical entity; (2) the number of compounds to be tested is extremely large; and (3) the beads are difficult to manipulate into 96-well microtitre plates.

To avoid the problems inherent in screening combinatorial libraries by the 96-well format, some have reported the use of simple homogeneous assays that could be described as "free-format". As an example, an assay using pigment cells (melanocytes) in a simple homogeneous assay for combinatorial peptide libraries was reported by Jayawickreme et al. in *Proc. Nat'l Acad. Sci. (USA)*, vol. 191, pp. 1614–18 (Mar. 1994). According to the authors, they placed cells under agarose in petri dishes, then placed beads that carried combinatorial compounds on the surface of the agarose and then partially released the compounds from the beads. The active compounds were visualized as dark pigment areas because, as the compounds diffused locally into the gel matrix, the active compounds caused the cells to change colors.

Another recent example is Daniel Chelsky's "Strategies for Screening Combinatorial Libraries: Novel and Traditional Approaches," reported at the *First Annual Conference of The Society for Biomolecular Screening* in Philadephia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change. Finally in *Molecular Diversity*, v. 2, pp. 57–63 (1996), Salmon, et al., reported a method similar to that of Jayawickreme et al., wherein combinatorial libraries were screened for compounds that had cytoxic effects on cancer cells growing in agar.

All three examples are variations of the time-tested gel assays for antibacterial or anticancer agents, and are also similar to the familiar immunological assays in which an antigen/antibody interaction is measured in a gel. Though these gel permeation assays were well-suited for screening bead-based combinatorial libraries, nobody has reported the extension of this format to heterogeneous assays or non-bead based libraries. Conventional wisdom discouraged investigators from testing the samples in a continuous format that could allow the samples to mix. Between the limited kind of assays reported and the concerns about the samples running together in a continuous format, only bead-based libraries have been assayed. Due to these limitations, investigators believed that the 96-well format was better suited for heterogeneous and non-bead based library screening. It would be desirable to conduct heterogeneous assays in a free format setting. Further, it would be desirable to test discrete compounds in a free format setting.

BRIEF SUMMARY OF THE INVENTION

The invention described herein, Continuous-Format High Throughput Screening (CF-HTS), successfully implements the free format concept for any assay, homogeneous or heterogeneous, that can be accomplished in the 96-well format. In addition, CF-HTS is also useful to screen combinatorial libraries with heterogeneous assays, not just homogeneous assays. Furthermore, CF-HTS can assay discrete compounds without the costs and complexities associated with miniaturization. Concerns regarding the potential that reagents and test results will run together during subsequent steps proved to be unfounded.

One embodiment of the invention relates to testing samples for a biological or biochemical activity by:
a) introducing multiple test samples into or onto a porous assay matrix that optionally contains one or more assay components;
b) using at least one matrix to introduce one or more assay component to the assay wherein the matrix may or may not be the porous assay matrix; and
c) performing the step of,
i) washing any matrix used in the assay to remove an excess amount of test sample, assay component or a combination thereof; or
ii) contacting any matrix used in the assay with an additional reagent in bulk solution or as a liquid.

Another embodiment relates to testing samples for a biological or biochemical activity by introducing multiple test samples into or onto a porous assay matrix that optionally contains one or more assay components, and using at least two additional matrices to perform the assay.

Yet, another embodiment relates simultaneously testing more than 96 test samples for a biological or biochemical activity by introducing the more than 96 test samples into or onto a porous assay matrix that optionally contains one or more assay components and performing the assay.

BRIEF DESCRIPTION OF THE DRAWINGS

FIG. 2 illustrates removal of the gELISA test sample matrix and the porous gel matrix, followed by washing and addition of liquid or solution reagents to form the reporter complex on the non-porous reagent matrix.

DETAILED DESCRIPTION OF THE INVENTION

Figure 1A:
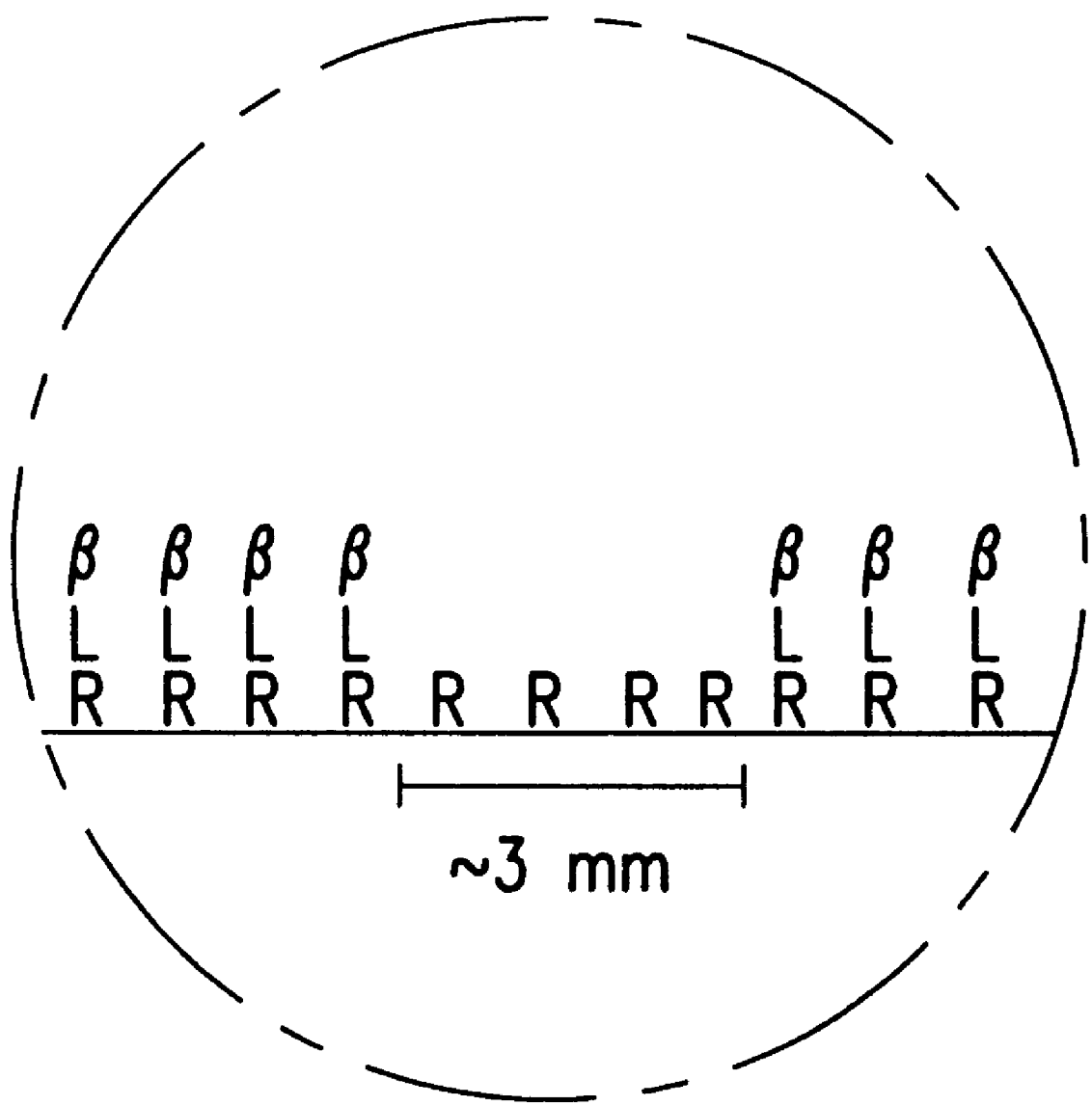
FIG. 1 illustrates gELISA test samples on a non-porous matrix contacting one side of a porous gel matrix containing assay reagent, which in turn, contacts a non-porous matrix carrying a further assay reagent.

The central idea behind CF-HTS is to place test samples in the context of a porous matrix. The method comprises placing one or more assay components within, on top of, or at the bottom of a matrix such as a gel, a plastic sheet, a filter or other forms of easily manipulated solid support. When samples are introduced to the porous matrix they diffuse sufficiently slowly such that the assays can be performed without the test samples running together. Thus, the CF-HTS format separates the test samples by diffusion rather by an impenetrable barrier. If one allows the tests to run too long, the test samples and results will eventually run together. However, when carefully timed, CF-HTS allows a very high density of compounds to be screened simultaneously, yet individually, without the need to fill individual wells or reaction containers with solvents or assay components. Furthermore, by manipulating matrices that carry the reaction components, one can perform even complex heterogenous assays in this format. The manipulation of matrices for heterogeneous assays is completely unprecedented and makes CF-HTS as flexible as the 96-well format in its ability to screen a wide range of biological or biochemical processes. Further, CF-HTS achieves the kinds of advantages anticipated by miniaturization without the commitant disadvantages, and has unique advantages.

CF-HTS employs a wide range of matrices and assay components. Matrices include but are not limited to gels composed of agarose, acrylamide, or other gelatinous materials, membranes, filters, and plastics. Matrices can be composed of materials including but not limited to polystyrene, polypropylene, other plastics, paper fiber, glass, glass fiber, silica, polycarbonate, polyester, polyvinylidene chloride and polyethylene. Matrices can be impermeable solids, porous solids such as filters, or gels. Assay components include but are not limited to macromolecules such as nucleic acids, proteins, and other synthetic or natural macromolecules; cells, cell lysates, biological extracts, organelles, and other complex biological entities and mixtures; and small molecules such as buffers, salts, inhibitors, substrates, peptides, dyes, nucleotides, cofactors, ions, and solvents.

A CF-HTS assay is an assay wherein multiple test samples or compounds are separated by diffusion rather than by impenetrable barriers. The critical component is the introduction of multiple (greater than 1) test samples into or onto a porous assay matrix that optionally contains one or more assay components. Porous assay matrices containing assay component(s) are prepared by adding, mixing, pouring, dispensing, or soaking components into the matrix. Porous matrices are also prepared by coupling, coating, binding, fixing, linking, conjugating or attaching assay components into or onto a surface of a matrix.

Furthermore, a porous matrix is also prepared by forming a thin film of solution or liquid on a bed of cells, enzyme or other immobilized assay component. The porous assay matrices are used to control the order and/or the duration of component addition, and the extent of mixing and diffusion when the assay components are combined.

CF-HTS may also use non-porous matrices. The non-porous matrices are prepared by coupling, coating, binding, fixing, linking, conjugating or attaching assay components or test samples onto a surface of the non-porous matrix. The use of non-porous matrices in CF-HTS spatially fixes one or more of the assay components.

When the assay components are introduced onto the surface of a matrix, the assay components are attached by covalent or noncovalent, specific or nonspecific interactions with matrices that are non-derivitized, derivitized or otherwise pre-treated to facilitate the attachment of assay components. After attachment, the assay component is spatially fixed so that it is immobilized for the purposes of the assay. In this case, either the test samples must be able to diffuse through a matrix to reach the assay components, and/or subcomponents or products of the assay components must be able to diffuse through a matrix to reach the test samples.

At least one porous matrix containing the test samples is used in any one or more of the following steps.

(1) Bringing the surface of the porous matrix in contact with at least one other (porous or non-porous) matrix such that the samples and/or one or more of the assay components can diffuse across the interface.

(2) Separating two or more matrices to halt interaction of components and/or samples.

(3) Bringing the surface of two or more matrices in contact such that the assay components can interact.

(4) Washing, rinsing, or eluting a matrix with liquid buffers or other solvents to remove unbound and/or nonspecifically bound assay components.

(5) Dispensing, pouring, adding, or soaking assay components in solution onto a matrix or filtering said components through a matrix.

(6) Imaging, reading, scanning, detecting, or otherwise visualizing the radiometric, fluorescent, spectrophotometric, or electromagnetic signals present on or in one or more matrix.

CF-HTS provides many advantages over the prior art. The absence of distinct wells eliminates the need to simultaneously and accurately dispense assay components or reagents into wells. Instead, the assay components are dispensed and mixed by homogeneous bulk handling. Since the assay components are prepared as a homogeneous bulk solution or martrix, there is minimal statistical sample to sample variation. By comparison, the presence of wells in the 96-well format creates large sample to sample variations.

Further, CF-HTS provides for extremely high density screening of large numbers of compounds. Even if the observed hits "run together" to a limited extent, one need to only retest the compounds that are located near the hit. Thus, if one were able to reduce 10,000 test samples to 50 candidates around a visualized area, one could easily reduce the 50 candidates to the active compound(s) with even the old 96-well technology.

By dispensing and drying discrete compounds onto plastic sheets in highly packed arrays, then applying them to CF-HTS, one addresses all of the critical miniaturization issues. This format requires no innovations in plastics or other materials to achieve miniaturization, because miniaturization is achieved simply by limiting the amount of sample that diffuses into the matrix. This format also does not require microfluidics to dispense assay reagents because the entire assay takes place, essentially in "one giant well" where reagents and solutions are handled in bulk. Only the test samples need to be dispensed by microfluidics. Moreover, much less statistical variation exists in this format because one only needs to look for localized zones of heterogeneity in the otherwise homogeneous matrix. One does not need to read and compare many different wells. In addition to all of the anticipated benefits of miniaturization (cost, throughput, reagent usage, test compound usage), CF-HTS also provides surprising benefits such as the ability to handle most steps of the assay in bulk.

A central aspect of CF-HTS is the observation that assay components and test samples do not rapidly diffuse laterally even at interfaces between matrices. For example, when an agarose gel is placed on a plastic plate, there is significant liquid at the interface on the surface of the gel. When an interaction is required between an assay component in the gel and an assay component on the plate (as in the ELISA example), it is critical that the component in the gel is able to diffuse out of the gel and onto the plate. However, CF-HTS requires the concomitant lateral diffusion to be considerably slower, so that the interaction on the plate is localized near the original location of the gel-based component. These same principles apply to any matrix-matrix interface between gels, filters, or surfaces (or any other matrix) in any combination. The realization that this diffusion behavior is controllable and is generally applicable to all matrix interfaces is unprecedented and contrary to conventional wisdom.

A preferred method for introducing test samples or compounds into a matrix (such as a gel or wetted filter) is to dispense and dry small volumes of each sample onto a surface, such as the surface of a plastic sheet in an array so that no two samples may mix or overlap, and each is in a specified location. When the plastic sheet is placed onto a matrix, the samples dissolve and diffuse into the matrix in locations corresponding to their predefined locations in the initial array.

An alternative method for dispensing samples into an array is to dispense the samples onto a porous matrix such as a filter where the volume of each sample dispensed is low enough so that samples do not overlap within the matrix. Upon contact with another porous matrix that contains more liquid, the compounds diffuse to initiate the assay.

A preferred method for introducing bead-based combinatorial compounds into a matrix is to dispense beads randomly or in an ordered array onto a surface, such as the surface of a plastic sheet. The beads can then be treated to release (cleave) the test compounds if they are covalently attached to the beads by a labile linker (photocleavage and gas-phase acid cleavage are well known in the art). Each compound is then noncovalently associated with the area occupied by its bead of origin, and the dry compounds can then be introduced into or onto a matrix.

An alternative method for introducing discrete compounds into a matrix is to soak or otherwise noncovalently attach each compound into or onto beads. Using this method, a large number of compounds can be mixed together once on the beads such that each bead still has a unique compound on it. Then, bead mixtures can be easily spread onto a surface for introduction to a matrix. This procedure completely eliminates the need for small volume liquid handling.

When the initial array of samples introduced into a matrix in a CF-HTS screen is high density, such that a particular zone of activity spatially covers the initial location of more than one sample, then each of these samples is potentially the source of the observed activity. For higher initial densities, there will be more candidate compounds for each zone as multiple compounds will be present in a particular zone. Compounds may diffuse together, but they will each still have their own spatial gradient and will not be quantitatively mixed at any one location. Therefore, the center of the zone will still correlate to the precise location of the active compound in the initial array. In practice, hits are rare enough that retesting multiple samples to ensure the identification of active compounds for each active zone is trivial.

An alternative embodiment of the invention is to introduce physical barriers (thus making the format non-continuous in the rigorous use of the word) into the matrices of an assay to limit the distance that samples can diffuse. For example, two gels containing an enzyme and substrate, respectively, can each be cut with a mesh ("cookie-cutter") such that each gel is subdivided into many discrete locations. Then one can still bring the two gels into contact so that the substrate and enzyme can diffuse together within each subdivided gel piece. Test samples could then be introduced to each subdivided gel piece so that the assays are completely independent with no diffusion between assays. This embodiment effectively eliminates some of the CF-HTS advantages by introducing statistical deviations between test samples and by fixing the volume and thereby limiting the signal for high density arrays. But, this embodiment would still reap the benefit of matrix based heterogeneous assays in which assay components do not need to be dispensed into a large number of parallel reaction vessels, and it eliminates the partial mixing of samples.

gGELISA

Enzyme linked immunosorption assays (ELISA) are heterogeneous assays which detect the binding between ligands in solution and immobilized receptors. ELISA requires many reagent mixing and washing steps that are difficult to perform in the 96-well format, and one could envision even greater difficulty when the wells are reduced from the 96-well format to the 384-well format. The inventors have applied the CF-HTS method for detecting inhibition of binding between ligands and immobilized receptor targets (gELISA).

A receptor is any molecule that can bind another molecule. Non-limiting examples are proteins, peptides, nucleic acids, carbohydrates and complexes of the foregoing examples. A receptor is immobilized on one of several possible matrices (the receptor matrix) including but not limited to plastic surfaces (e.g., petri dish or plastic plate (from Nunc)), membranes or filters which have high target binding capacity (e.g., nitrocellulose, nylon, or PVDF (Millipore, Corning Costar, Schleicher & Schuell, BioRad) or derivatized membranes such as SAM membranes (Promega)). A porous ligand matrix (e.g., agarose gel or porous membrane) is prepared such that the ligand for the immobilized receptor is dispensed on or into the matrix. Test compounds or samples are dispensed directly onto the ligand matrix, or alternatively, on or into a test sample matrix (e.g., polystyrene (Tekra), polyvinylidene (e.g., from Dow Brands) or other flexible plastic sheet or membrane. The test matrix is brought in contact with the ligand matrix and the samples are allowed to diffuse into the ligand matrix. After a suitable incubation period, the ligand matrix is brought into contact with the receptor matrix, allowing the ligand and the samples to come in contact with and potentially reacting with the receptor by diffusion (FIG. 1 shows immobilized receptor R binding to biotinylated ligand Lβ). During incubation, ligands will bind to the immobilized receptor unless a sample compound inhibits the ligand/receptor binding.

Figure 3:
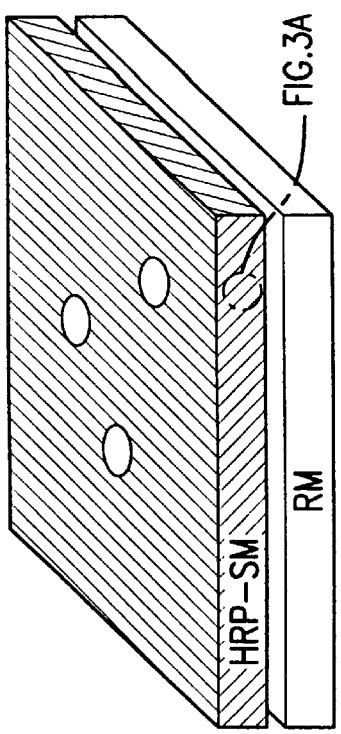
FIG. 3 illustrates visualizing the gELISA assay by contacting the reporter complex matrix with a porous gel matrix containing the reporter substrate.
Figure 3:
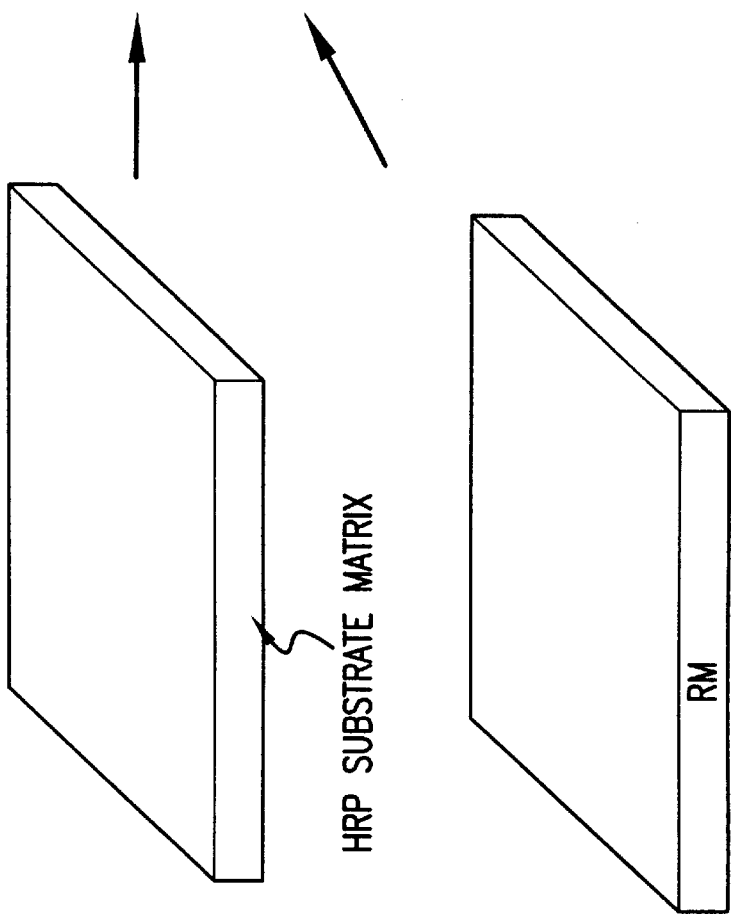
Figure 3A:
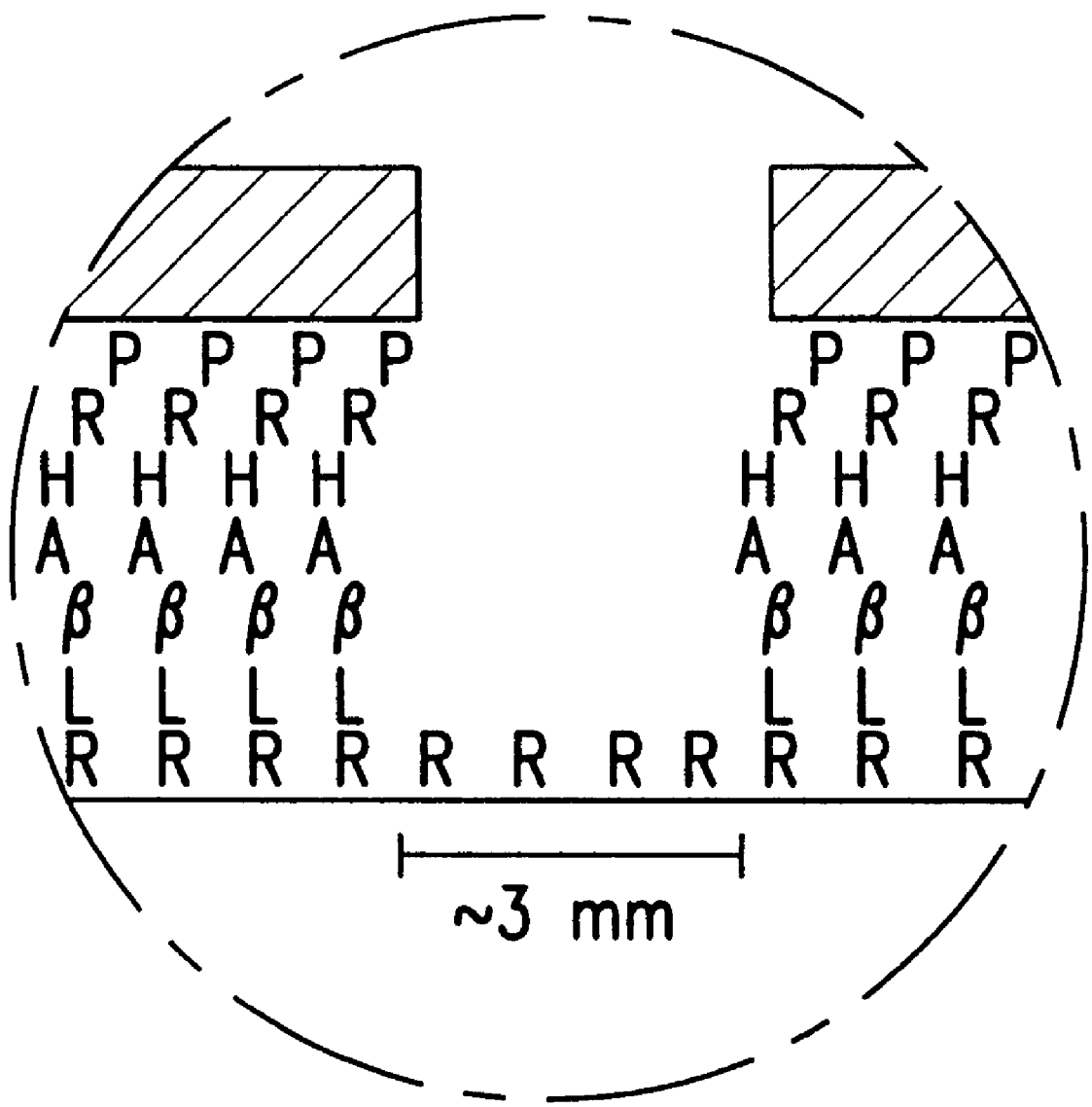

After a suitable incubation period, the receptor matrix is removed and washed with a suitable buffer to remove unbound and non-specifically bound ligand and samples. The receptor matrix is then soaked in a solution containing assay reagents that will interact with the ligand (e.g., an antibody, avidin or streptavidin in the case of a biotinylated ligand) and has the ability to be detected either directly (e.g., by fluorescence or radioactivity) or indirectly (e.g., horse radish peroxidase (HRP), alkaline phosphatase (AP), or betagalactosidase conjugate) (FIG. 2 shows an avidin-HRP conjugate, AHRP, attached to the biotinylated ligands). After suitable incubation, the receptor matrix is removed from the solution and washed to remove unbound and non-specifically bound reagent. In the case of direct signal detection the matrix is imaged using the appropriate method (e.g., spectrophotometric scanners, CCD cameras, film, phosphorimagers, or scintillation detection devices). Indirect signals (e.g., HRP or AP) require an additional signal development reaction, achieved by dispensing substrates or other necessary reaction components in or onto a porous substrate matrix and placing this matrix in contact with the receptor matrix. The enzyme (e.g., HRP or AP) then reacts with the substrate (FIG. 3). Alternatively, a precipitating substrate is introduced in solution instead of in a matrix. Under any visualization method, the ligand/receptor binding areas will produce a visible reaction, while the areas where ligand/receptor binding was inhibited will not produce a visible reaction.

Cell/Ligand Binding

CF-HTS can also be used to detect the inhibition of ligand/cellular receptor binding. In the traditional assay, one combines a test compound, radiolabeled ligands and cells that express the corresponding receptor in a vessel such as a well. Then, sufficient time is provided to allow the receptor to bind the ligand, if such binding has not been inhibited by the test compound. Any unbound and non-specifically bound components are removed from the cells, and the amount of radioactivity associated with the cells are measured. The inventors have adopted CF-HTS method to detect inhibition of ligands binding to cells.

Figure 4A:
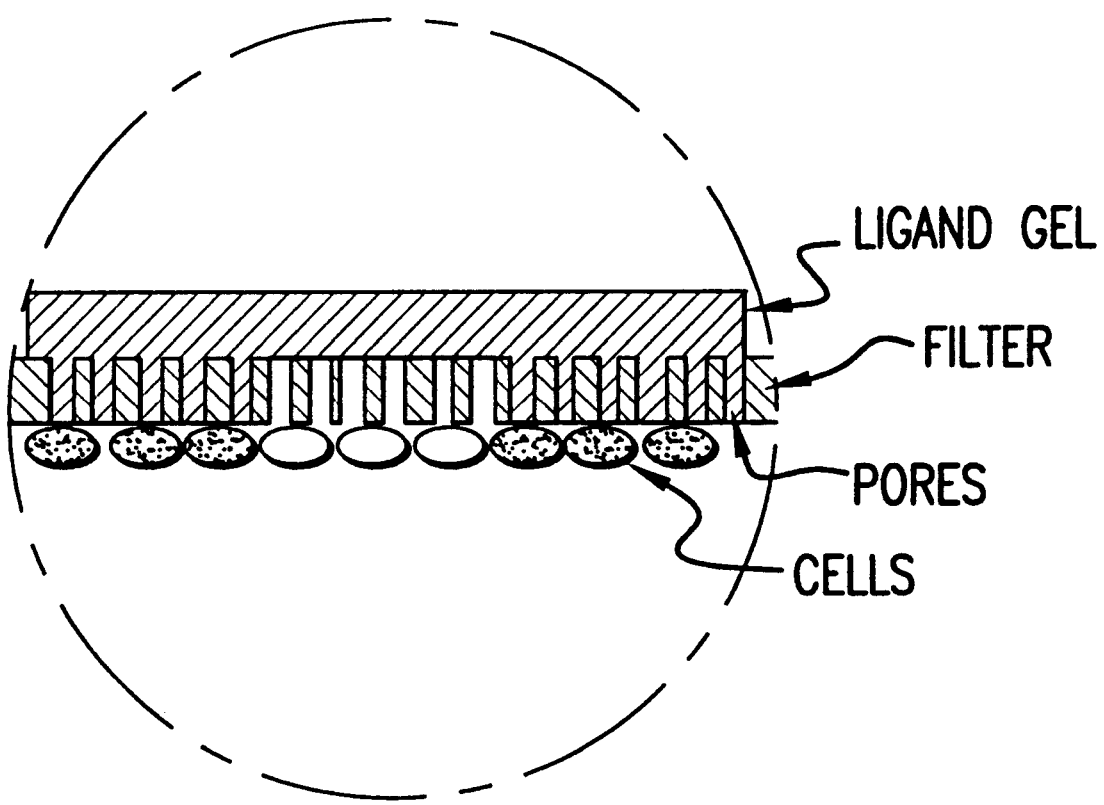
FIG. 4 illustrates how a ligand matrix is applied on the filter surface opposite that of the filter surface carrying cells.

Cells expressing the desired receptor are grown or plated on a matrix (cell matrix) such as but not limited to gels, filters, or membranes (e.g., Transwell tissue culture membranes (Corning Costar) or chemotaxis membranes (Neuro Probe)). A porous matrix (e.g., agarose gel or porous membrane) is prepared such that labeled ligand for the receptor is dispensed on or into the matrix (ligand matrix). Test compounds or samples are dispensed directly onto the ligand or cell matrix, or alternatively on or into another matrix (e.g., polystyrene (Tekra), polyvinylidene or other flexible plastic sheet or membrane; sample matrix). The sample matrix is brought in contact with the ligand matrix thereby allowing the sample to diffuse into the ligand matrix. After a suitable incubation period, the ligand matrix is brought into contact with the cell matrix, preferrably on the non-cell side of the matrix, and allowing the ligand and sample to contact and react with the receptor by diffusion (FIG. 4). During incubation, the labeled ligands will bind to the immobilized cells unless a sample inhibits the ligand/cell binding.

Figure 5:
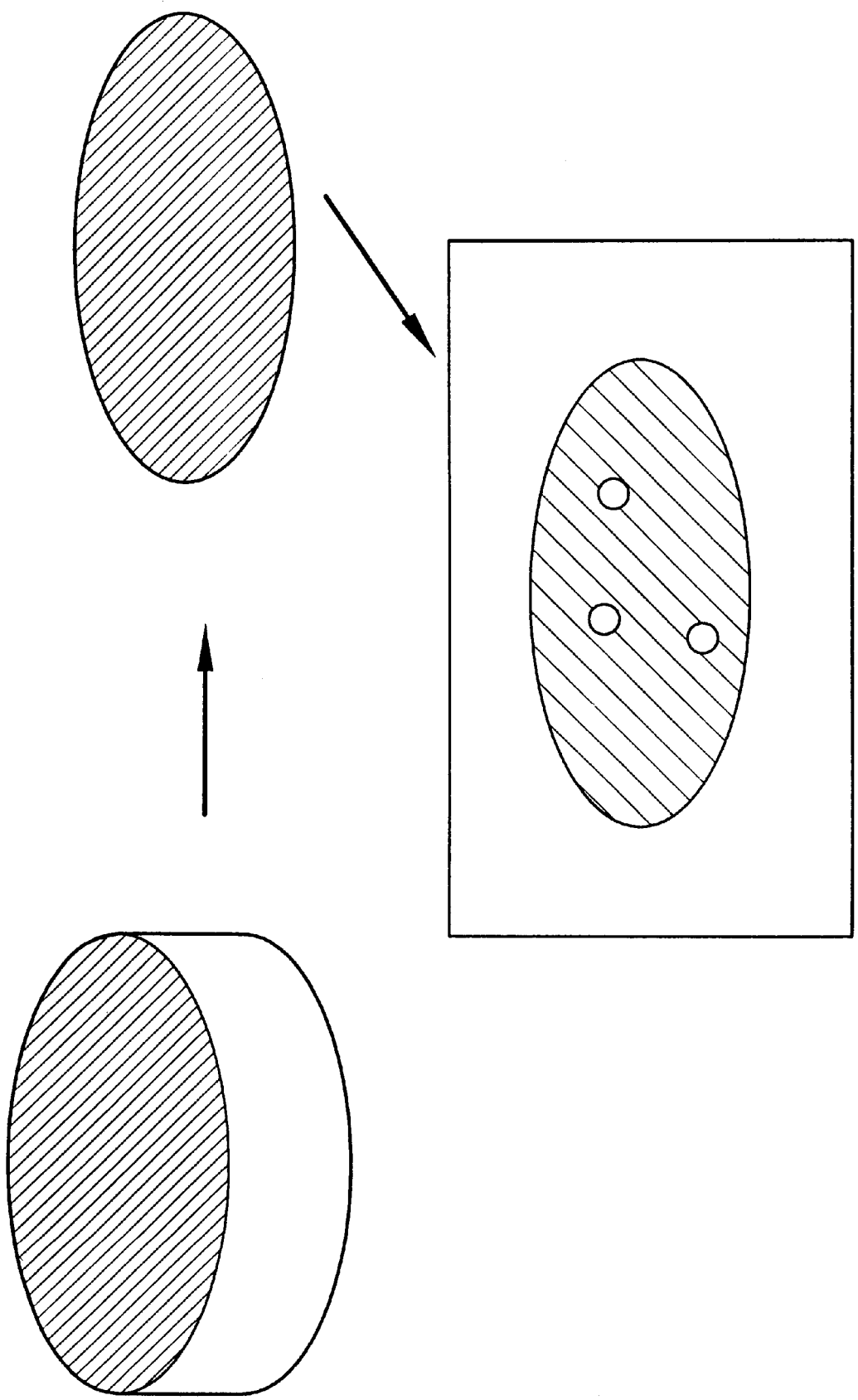
FIG. 5 illustrates what a filter surface carrying cells may produce when the assay is visualized.

After incubation, the cell matrix is separated from the ligand matrix and washed with a suitable buffer to remove unbound and non-specifically bound ligands and samples. The cell matrix is imaged using the appropriate method (e.g., spectrophotometric scanners, CCD cameras, film, phosphorimagers, or scintillation detection devices) (FIG. 5 illustrates development of the assay on a film).

As shown above, CF-HTS achieves all of the advantages envisioned for the "free-format" assays, and can be applied to all different types of biological or biochemical assays, under all different types of formats, and with all different reagents and equipment. Because of its broad applicability, it is best illustrated by the following examples. However, these examples illustrate the preferred embodiment of the present invention, and do not limit the claims or the specification. The ordinary artisan will readily appreciate that changes and modifications to the specified embodiments can be made without departing from the scope and spirit of the invention. Finally, all citations herein are incorporated by reference.

EXAMPLES

Example 1

A Two-Step Colorimetric Gel Assay for Detecting Phosphate Generated by Vancomycin Resistant Enzyme VanA VanA is a key enzyme in vancomycin resistance, and catalyzes the attachment of D-Alanine to D-Alanine or D-Alanine to D-lactate. Traditionally, this enzyme is assayed by generating color from phosphate that is released when the enzyme is active (VanA activity hydrolyzes ATP to ADP and phosphate). Scientists know that D-cycloserine inhibits VanA in a dose-dependent manner, and use this inhibitor as a positive control against other potential inhibitors.

Enzyme Gel

An enzyme gel was prepared by adding VanA enzyme to melted 1% agarose (high melting agarose, Gibco BRL) at 45° C. in 50 mM HEPES (N-[2-hydroxyethyl]piperazineN'-[2-ethanesulfonic acid]), 20 mM $MgCl_2$, 20 mM KCl, pH 7.3 to a final VanA concentration of 2 μM. This agar mixture was then poured into a BioRad gel casting apparatus and allowed to solidify at 2–8° C. for 30 minutes.

Substrate Gel

A substrate gel was prepared by adding ATP, D-Alanine and D-lactate to melted agarose to bring each component to 1 mM, 1.5 mM and 1.75 mM respectively, and preparing the gel as described for the enzyme gel.

Sample Matrix

A series of 1 μl aliquots of serial dilutions of 5000, 2000, 1000, 500, 200, 100 μM D-cycloserine, a known inhibitor used as a control sample, in 1:1 ethanol-water was dispensed on a piece of polyvinylidene chloride film (PVDC) and allowed to dry for 10 minutes.

Incubating the Enzyme with the Substrate in the Presence of Inhibitor

The enzyme gel was brought in contact with the sample matrix for 5 minutes. Then the substrate gel was placed on top of the enzyme gel and allowed to incubate for 15–20 minutes. Subsequently, the two gels were separated. During incubation, one expects phosphate to be produced throughout the gel as the enzyme catalyzes the attachment of the substrates, with the exception of the zones where D-cycloserine was concentrated enough to inhibit the reaction.

Visualizing the Assay

A phosphate detection cocktail consisting of freshly prepared 0.15% Malachite green and 1.4% Ammonium Molybdate in 1.33N HCl was poured and uniformly distributed onto the enzyme and substrate gels. These reagents react with phosphate and generate increasingly dark shades of green as a function of increasing concentrations of phosphate.

Figure 6:
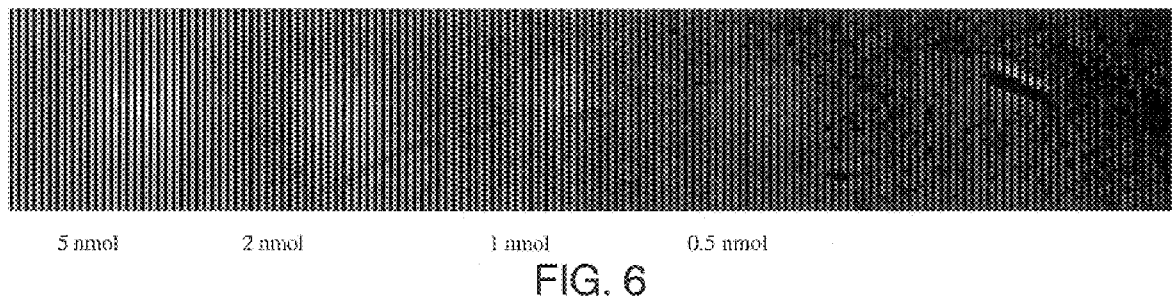
FIG. 6 shows the result of a VanA assay using varying concentrations of a known dose-dependent inhibitor.

Color was allowed to develop for 5–10 minutes (FIG. 6 illustrates color development on the gel where inhibitor amounts varied from 5 nanomole to 0.5 nanomole). The green colored gels were photographed using a Stratagene Eagle Eye CCD camera. As expected, the degree that inhibitory zones looked less green correlated to the concentration of inhibitor added. This assay can therefore be used to screen for inhibitors of VanA by arraying combinatorial beads or compounds dispensed onto any other surface which is then brought into contact with the gel assay.

This assay also demonstrates that the gel screening format is amenable to multiple step reactions. This feature is necessary for this format to be useful with a wide range of assays, because many assays require multiple steps. In this case, the VanA assay is a two step assay of enzymatic activity followed by color development. Homogeneous (single step) versions of this assay are not readily feasible because the color development reagents and conditions interfere with VanA activity, and are also incompatible with delivery in an agar gel. Therefore, the spatial and temporal separation of these two steps by first having an enzymatic gel assay followed by a solution-phase color development step is desirable.

Example 2

A two-step gel assay for detecting phosphate generated by S. Cerevisiae Elongation Factor 3 ATPase activity stimulated by Ribosomes binding When fungal elongation factor 3 (EF-3) interacts with ribosomes, phosphatase activity is stimulated. The inventors have applied CF-HTS to the assay for this activity.

Figure 7:
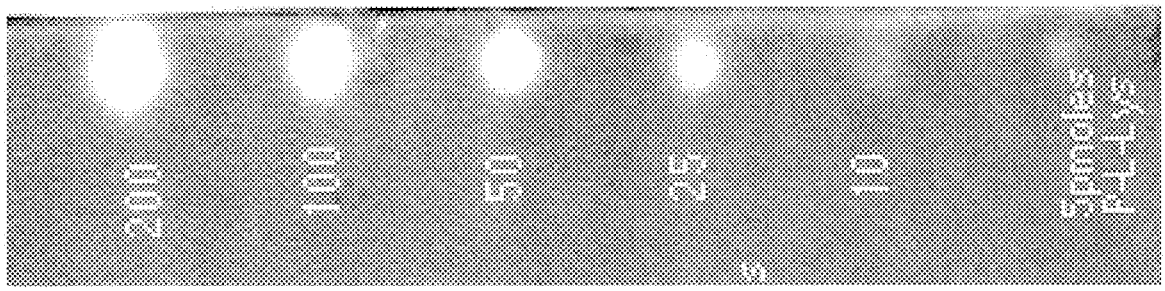
FIG. 7 shows the result of a EF-3 assay using varying concentrations of a known inhibitor.

An enzyme gel containing EF-3 (a highly temperature sensitive enzyme) and yeast ribosomes in EF-3 assay buffer was prepared. A substrate gel containing 1 mM ATP in assay buffer was also prepared. Both gels contained 2% dimethyl sulfoxide in low melting agarose (Gibco BRL), and were prepared at 37° C. and allowed to set for 30 minutes at 4° C. Serial dilutions of Poly-L-lysine, an inhibitor of EF-3 used as a control sample, was spotted onto PVDC film and dried (sample matrix). The assay was then conducted as in Example 1 by pre-incubating the enzyme gel with the inhibitors on the sample matrix. Then the enzyme gel was placed in contact with the substrate gel for 20 minutes. As in Example 1, the enzyme and substrate gels were stained with Malachite green/Ammonium Molybdate color development cocktail. Then the enzyme gel was imaged with a CCD camera. The inhibitor spots appear as clearer zones in a green background. FIG. 7 illustrates color development on the gel where inhibitor amounts varied from 5 picomole to 200 picomole. The results show the dose dependent signal of the inhibitor, indicating that compounds can be screened in this assay to discover new EF-3 inhibitors. Example 2 demonstrates the utility of CF-HTS even with the complexity introduced by the presence of organelles or other crude biological mixtures or extracts.

Example 3 gELISA Indirect Color Detection of Protein-Protein Interaction Inhibitors

As discussed above, ELISA is commonly used to detect inhibition of ligand-receptor interactions where the receptors are immobilized in microtitre wells. "Ligand-receptor" pairs used in ELISA can comprise any pair of binding molecules from proteins or other macromolecules to small molecules. These assays are complex, multiple-step assays that require immobilizing the receptor, incubating receptor with ligand, washing to remove unwanted nonspecifically retained ligand that would otherwise cause high signal background, binding visualizing reagents (e.g., a ligand specific antibody conjugated to a reporter enzyme) to the receptor-bound ligand and generating a visible signal by providing substrates for the reporter enzyme. It is apparent that the complexity of ELISA has led the HTS industry to conclude that ELISA cannot be adapted into a free-format assay. Nevertheless, the inventors have adapted this complex multi-step assay to the CF-HTS format to assay a variety of protein-protein, protein-ligand, and other ligand binding interactions.

Urokinase-type plasminogen activator (uPA) binds to its corresponding receptor (uPAR). The uPA/uPAR interaction has been implicated in the metastasis of various types of cancers. The inventors have adapted a traditional uPA/uPAR ELISA to CF-HTS using purified receptors and ligands.

uPAR Matrix

Plastic plates (7.5 cm×11.5 cm; from Nunc, Inc. Naperville, IL) were coated overnight with 15 mls of 118 nM purified uPAR in phosphate buffered saline (PBS) (Life Technologies, Grand Island, N.Y.) at pH 7.4 and 4° C. After coating the plastic plate overnight, the uPAR solution was decanted, and the remaining binding sites on the plastic plate were blocked by adding 15 mls of PBS containing 1% (w/v) casein and incubating for 2 hrs at room temperature (RT). After blocking, the blocking solution was decanted and the plastic plate was washed five times with 20 mls of wash buffer consisting of 0.05% Tween-20 (polyoxyethylenesorbitan monolaurate) in PBS. After washing the plastic plate was dryed for 10 minutes at RT. This was timed so that the plastic plate could be shortly thereafter used in the assay described below to avoid overdrying the matrix which may lead to loss of activity.

β-uPA Matrix

For the purposes of the assay, the uPA used is labeled with biotin (β-uPA). Gels containing β-uPA were prepared by soaking β-uPA into agar to avoid high temperatures (as opposed to pouring it into molten agar in Examples 1 and 2). The agar was prepared by first mixing 0.1 g of agarose (Sigma, St. Louis, Mo.) with 10 ml PBS, heating until molten, and then casting in 8×7×0.075 cm$^3$ gel apparatus (Bio-Rad, Hercules, Calif.). Upon solidification (either at room temperature or 4° C.) the gels were soaked overnight at 4° C. in 15 mls of β-uPA (about 10 nM) in assay buffer consisting of PBS, 0.05% Tween-20 and 0.1% casein (both from Sigma, St. Louis, Mo.). The gel was dried for 20 minutes at RT just before use.

Sample Matrix

In the absence of a known small molecule inhibitor for the uPA/uPAR binding, a non-biotinylated uPA (Pro-uPA) was used as a control sample inhibitor of β-uPA/uPAR binding. Five microliters aliquots of 0, 0.03, 0.1, 0.3, 1, and 3 μM pro-uPA in assay buffer were dispensed on a PVDC film (Dowbrands L.P., Indianapolis, IN) and dried for 2 hr at RT.

Incubating the uPAR with Pro-uPA and β-uPA The sample matrix was placed on one side of the β-uPA gel with the dry pro-uPA spots in contact with the β-uPA gel surface. The pro-uPA was allowed to diffuse into the gel for 10 minutes at RT. Subsequently, the other side of the β-uPA gel was placed in the plastic plate to allow the β-uPA (acting as a ligand) and the pro-uPA (acting as a competitive inhibitor) to interact with the uPAR on the surface of the plastic plate. The binding/competition reaction was incubated for 20 minutes at RT. After incubation, the plastic plate was separated from the gel, and quickly washed 4 times with 20 ml of wash buffer. An avidin-horseradish-peroxidase (avidin-HRP) conjugate solution was prepared by diluting avidin-HRP (Sigma, St. Louis, Mo.) 1 to 25,000 in assay buffer and adding 15 ml to the plastic plate. The reaction was incubated for 10 minutes at RT followed by decanting of the avidin-HRP solution and washing of the plastic plate as above. The plastic plate was allowed to dry for 20 minutes.

The avidin in avidin-HRP binds specifically to biotin so that only the areas of the matrix that exhibit "ligand/receptor" binding will eventually exhibit color development. The areas of the matrix where "Iigand/receptor" binding is competitively inhibited by pro-uPA will not exhibit color.

Color Development

The color developing gel containing a colorimetric HRP substrate (OPD gel) was prepared by dissolving 2 o-phenylenediamine HCl (OPD) tablets into 7 mls of diluent (both from Abbott kit no. 6172-30, Abbott Labs, Abbott Park, Ill.) and combining this solution with an agarose solution made by melting 0.1 g agarose in 3 ml water. The final 10 ml mixture was cast in a 8×7×0.075 cm mini-protein II gel apparatus and allowed to solidify at 4° C. for 15 minutes. The gel was transferred from the glass plates of the gel casting stand to either PVDC or a flexible plastic sheet and allowed to air dry for 10 minutes at RT. The gel was then transferred to another PVDC or plastic sheet to allow the other side to dry for minutes. Then the OPD gel was placed in the plastic plate to begin color development. At various times during the OPD incubation, the plastic plate was placed on top of a 440 nm band pass filter (Omega Optical, Inc., Brattleboro, V.T.) which in turn was on top of a fiber optic diffusion plate illuminated by a Fiber-Lite light source (both from Dolan-Jenner Industries, Inc., Lawrence, Mass.). The resulting images were acquired with a CCD camera (Eagle Eye system, Stratagene, La Jolla, Calif.).

Control Experiment

Figure 8A:
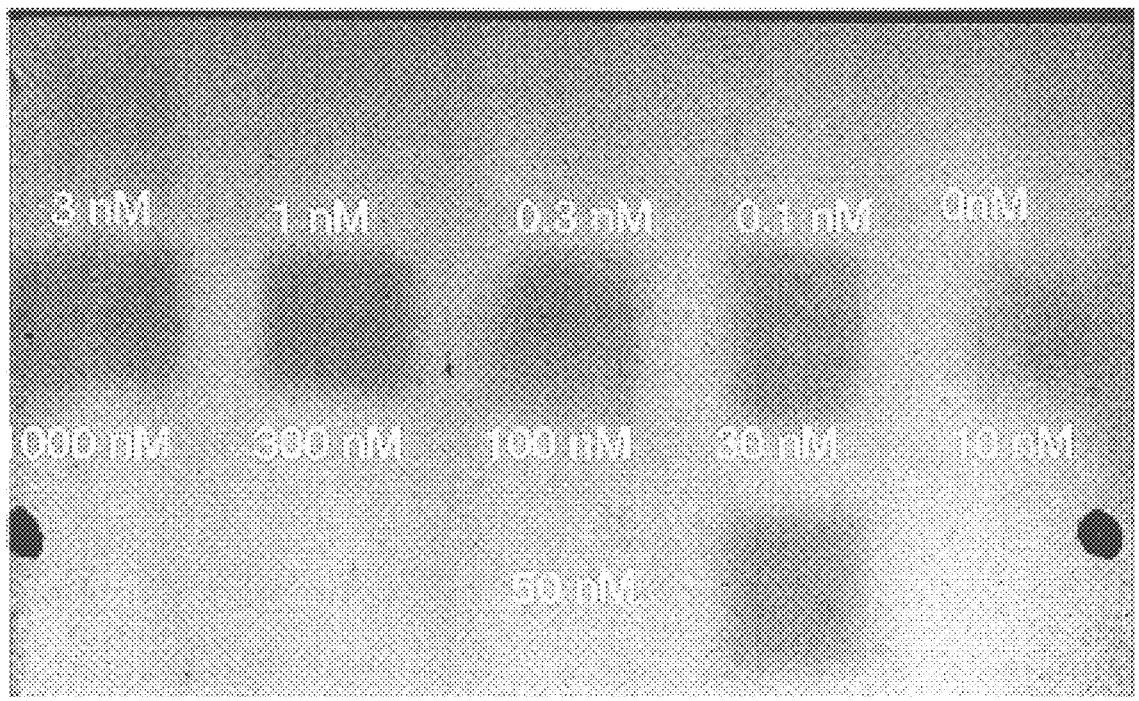
FIG. 8 illustrates a control experiment for gELISA assay for protein-protein interaction.
Figure 8B:
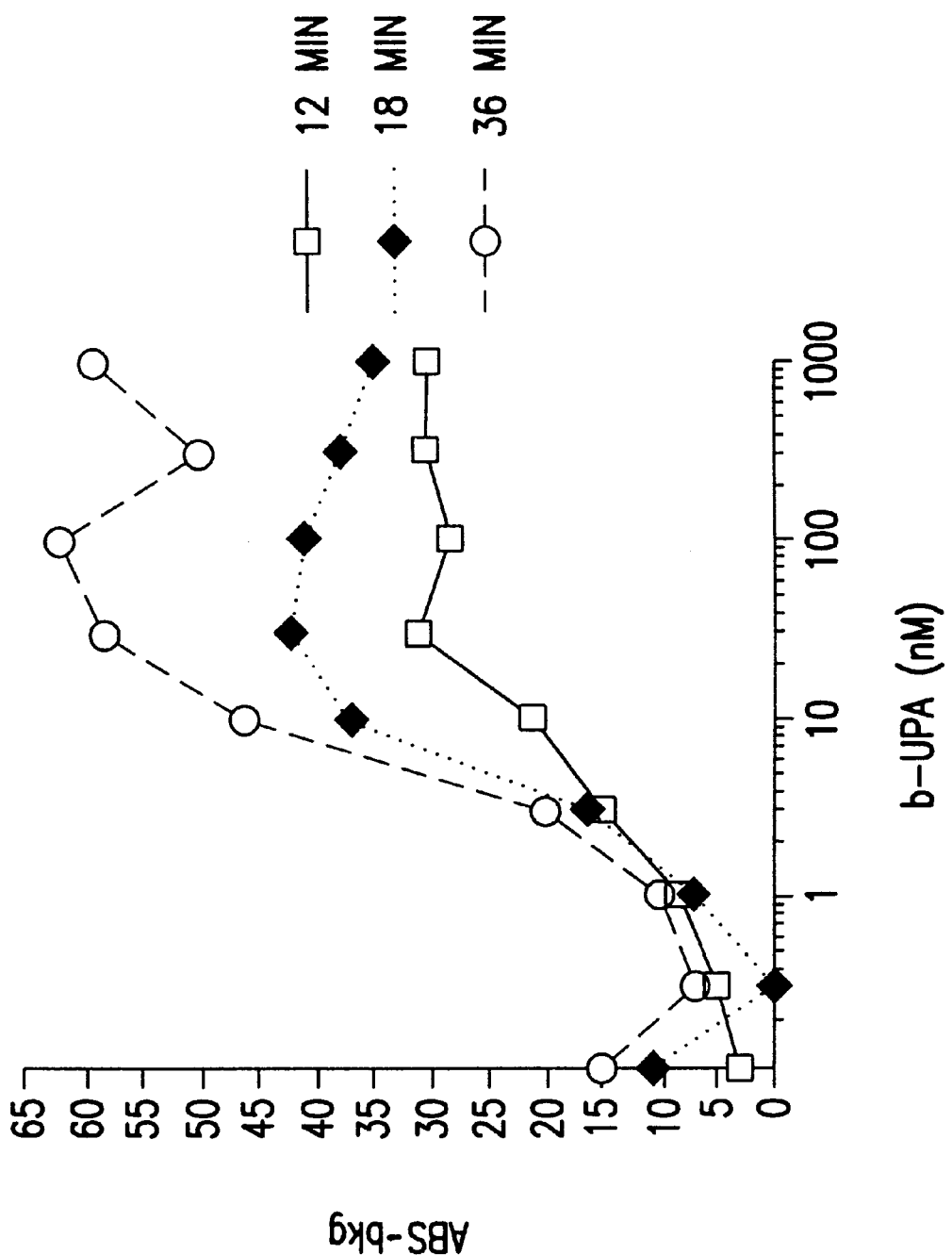

FIG. 8 illustrates a control experiment for Example 3. For FIG. 8A, agarose squares (1 cm$^2$) were soaked in solutions of various β-uPA concentrations as indicated beneath each square (except for the 50 nM solution which is labled to the left of the agarose sqaure). After the agarose squares were incubated on a uPAR immobilized plastic plate, they were removed. Then the plastic plate was washed and the areas of the matrix where β-uPA/uPAR binding occurred was visualized as described above. FIG. 8B shows a plot of the average pixel value (minus background) for each square (as determined by analyzing the digital image from the CCD camera with NIH Image Analysis software) against concentration of β-uPA in each agarose square at various times during OPD color development. The β-uPA delivered from the agarose gel showed a typical receptor-ligand binding curve with half-maximal binding (Kd) around 3–5 nM which is consistent with reported values for this reaction in standard ELISA and other assays which measure this parameter. FIG. 8 demonstrates that the indirect calorimetric signal generated by gELISA is quantitively dependent on the extent of ligand-receptor interaction.

Results of Pro-uPA/β-uPA Competition

Figure 9A:
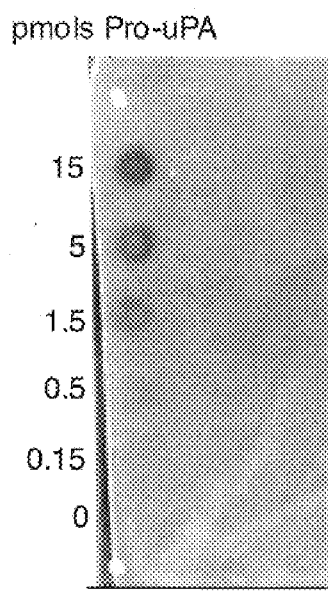
FIG. 9 illustrates the gELISA result of "inhibition" of protein-protein interaction.
Figure 9B:
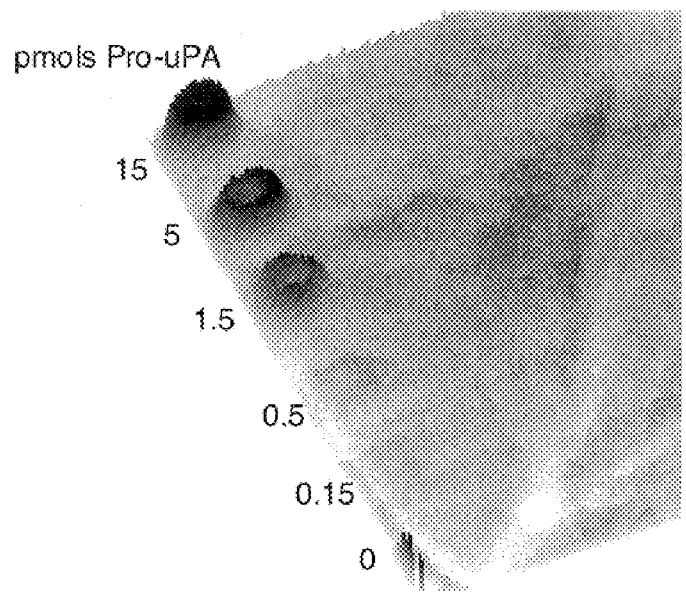

FIG. 9 demonstrates inhibition of β-uPA/uPAR binding by Pro-uPA. The spots in FIG. 9A indicate areas where β-uPA/uPAR binding was inhibited. Accordingly, the avidin-HRP did not bind in these areas. Consequently, the HRP did not react with the substrates in the OPD gel to generate color development. FIG. 9B is an alternative way of displaying these same CCD image data which enhances the ability of the human eye to see the quantitive titration.

Example 4

Direct Radiometric Detection of Inhibitors of Protein-Protein Interactions

T-cell activation is a component of the body's immune response. For downstream events to occur during T-cell activation, p56lck (LCK, a protein) must interact with the ITAM region (immunoglobulin related tyrosine based activation motif) of the cytoplasmic domains of the T-cell antigen receptor. Compounds that inhibit this protein-protein interaction are potential immunosuppressants. The inventors have used CF-HTS to assay this protein-protein interaction, where the LCK is immobilized to a membrane.

LCK Matrix

Biotinylated LCK is immobilized on a biotin capture membrane (SAM membrane) (Promega Corp., Madison, WI) by flooding a 11 cm×2 cm strip with 5 ml of 3 μM LCK in PBS containing 5 mM DTT (dithiothreitol) for 10 minutes at RT, after which the buffer is removed. This is timed so that the SAM membrane could be used shortly thereafter (within minutes) in the assay described below.

ITAM* Matrix

An agarose gel containing radiolabeled ITAM peptide (ITAM*) is prepared by mixing 0.1 g agarose with 10 ml buffer, heating until molten, and then casting in a 8×7×0.075 cm gel apparatus. The ITAM* is added either just before casting or alternatively soaked into the gel after solidification to a final concentration of 10 nM.

Sample Matrix

Test samples to be screened are dispensed onto a plastic surface or PVDC and dried to form the sample matrix.

Incubating the ITAM*. LCK and the Test Samples and Visualization

The sample matrix is brought into contact with one side of the ITAM* gel so that the test samples can diffuse into the ITAM* gel. Subsequently, the other side of the ITAM* gel is brought into contact with the SAM membrane on which the LCK has been immobilized. After incubating for 15–45 minutes, the SAM membrane is removed, washed, and imaged with a phosphor imager or film. Inhibitors of the ITAM-LCK interaction are indicated by zones of lower radioactivity that correspond to lower signal intensity on the image.

Control Experiment for ITAM*/LCK Binding

Agarose gels were prepared by mixing 0.1 g agarose with 10 ml buffer, heating until molten, and then casting in a 8×7×0.075 cm gel apparatus. After solidifcation, 1 cm diameter circles were punched out of the gel and soaked in 400 μl of 0. 1, 0.3, 1, 3, 10, and 20 nM $^{125}$I labeled ITAM (Amersham, Arlington Heights, Ill.) in buffer overnight at 4° C. The gel circles were removed from solution and allowed to dry for 20 minutes at RT. Then they were placed on the LCK-immobilized SAM membrane and incubated for 45 minutes at RT. The gels were removed and the membranes washed 4 times with buffer. After drying the SAM membranes were imaged using a phosphor imager.

Figure 10:
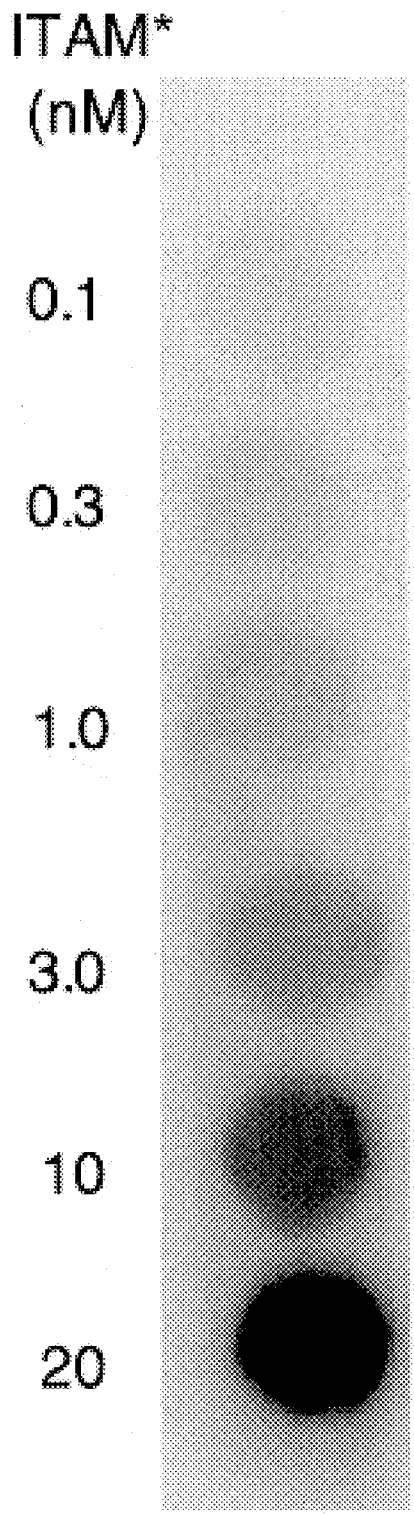
FIG. 10 shows the dose-dependent binding of radiolabeled ITAM to immobilized LCK.

FIG. 10 indicates a dose dependent binding between $^{125}$I-ITAM and immobilized LCK on the SAM membrane.

Figure 11:
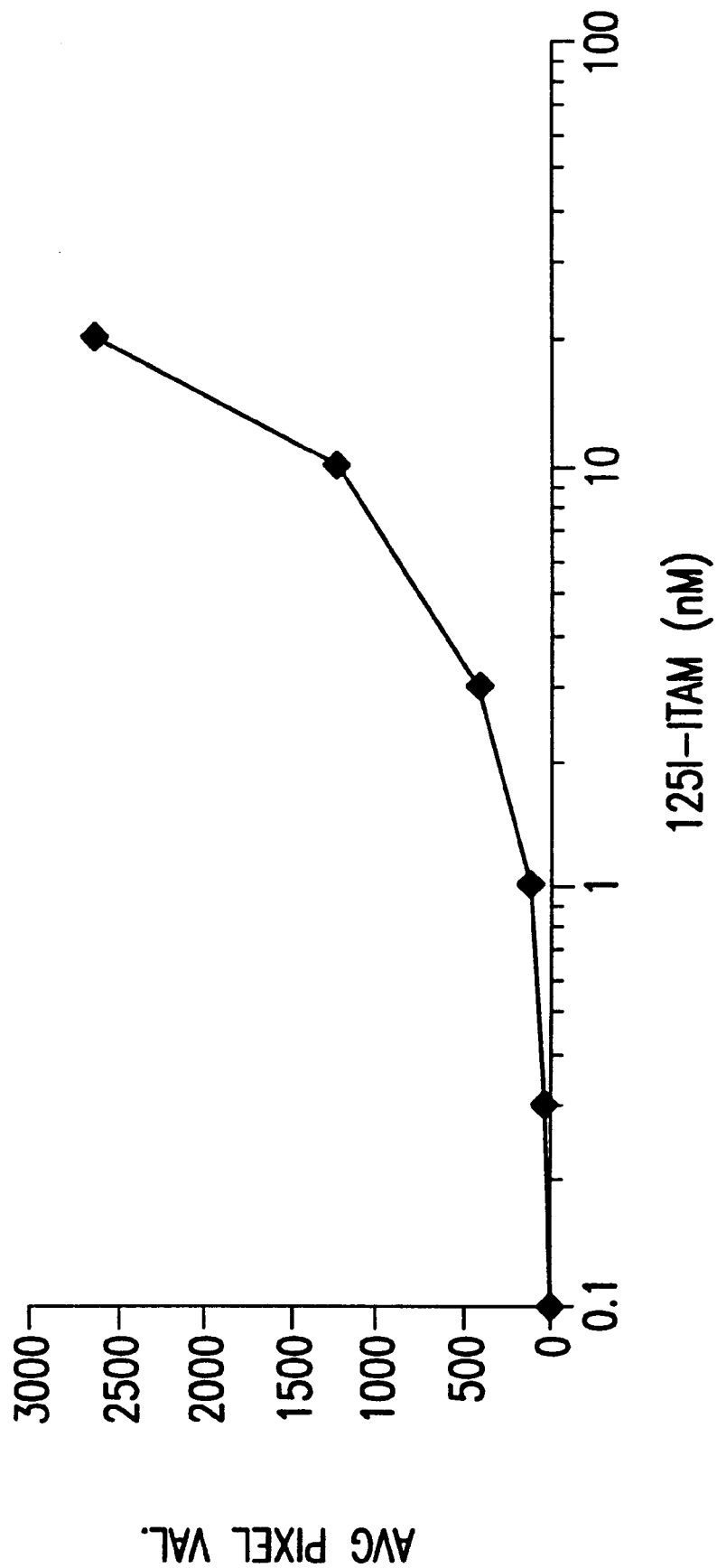
FIG. 11 charts the pixel values against ITAM concentration to show a typical receptor-ligand binding curve.

FIG. 11 shows a plot of the average pixel value (minus background) for each $^{125}$I-ITAM gel (as determined by analyzing the digitized image from the phosphor imager with ImageQuant software from Molecular Dynamics)

against $^{125}$I-ITAM concentration in the gel circle. The $^{125}$I-ITAM delivered from the gel to immobilized LCK showed a typical receptor-ligand binding curve.

Example 5
Whole-Cell Reporter Gene Assay Using a Combination Gel/Filter Format

Kidney cells, known as HEK cells, are transfected with a plasmid that contains a Cyclic-AMP Response element (CREB) promoter fused to a luciferase gene (luciferase reporter gene from Promega). When the transfected cells are treated with forskolin, luciferase reporter gene expression is induced. Thereafter, when a biological buffer containing the luciferase substrate (beetle luciferin from Promega) and appropriate co-factors (20 mM Tricine pH 7.8, 0.1 mM EDTA, 33 mM DTT, 0.3 mM Coenzyme A, 0.5 mM Adenosine Triphosphate, and 1 mM MgCl$_2$) is added to the HEK cells, a photon emission is generated that can be detected by conventional instrumentation. The inventors have adapted this assay to CF-HTS.

Cell Matrix

Cells in culture are treated with trypsin, transferred into a Coming/Costar TRANSWELL™ membrane (3 micron polycarbonate filter with a plastic support ring) and incubated overnight at 37° C., 5% CO$_2$ in the presence of tissue culture medium. Then the medium is removed from the membrane and the filter to which the cells are attached was air dried for 15 minutes and used shortly thereafter in the steps below.

Inducer Matrix

A gel containing the inducer of luciferase expression is prepared by adding 12 μl of a 10 mM stock of forskolin (Sigma stock in ethanol) into 6 mls of a 1% low-melting temperature agarose gel. The gel is solidified at room temperature with forskolin at a final concentration of 20 μM.

Sample Matrix

Samples that may block forskolin induction are dispensed and dried in discrete locations on PVDC at high density.

Incubating the Reagents and Detecting Inhibition

The inhibitor side of the PVDC is incubated with the inducer gel. Next, the gel containing the forskolin inducer is placed on the non-cell side of the cell matrix prepared above. These are incubated together at 37° C. at 5% CO$_2$ for 20 minutes. Then the forskolin gel is removed and the cell matrix is incubated at 37° C. at 5% CO$_2$ for an additional four hours for maximal expression of the luciferase construct. To detect the luciferase enzymatic activity (or inhibition thereof), the cell matrix filter is physically removed from its plastic support ring and placed into a petri dish. The petri dish is flooded with the luciferase substrate (beetle luciferin from Promega) in a biological buffer with appropriate co-factors to generate light as a signal. Because the signal is localized inside immobilized cells expressing luciferase, inhibitors of the initial induction step will result in zones of lower photon emission.

Example 6
Gel/Filter CF-HTS to Directly Detect Inhibitors of Ligand-Cell Interactions Ligand/receptor binding on cell surfaces initiates signal pathways in cells that ultimately lead to functional responses (e.g., cell proliferation or secretion of biologically active substances). To regulate the biological response of cells in disease states, one often seeks to inhibit ligand binding to cell surfaces. A common method for evaluating inhibitors of ligand/cellular receptor binding is to evaluate the ability of the inhibitor to reduce the binding between the radiolabeled natural ligand and the cells. This involves incubation of the cells with radioligand and inhibitor, followed by removal of unbound and non-specifically bound radioligand by washing, then measuring the amount of bound radioactivity.

Interleukin-8 (IL-8) is a chemotactic chemokine involved in inflammation by binding to receptors on various types of cells. The inventors have developed a CF-HTS ligand-receptor cell assay to evaluate inhibitors of this interaction.

Cell Matrix

HEK cells (ATCC, Bethesda, M.D.) expressing the IL-8a receptor were plated on a 75 mm diameter transwell membrane filter (Corning Costar Corp, Cambridge, Mass.) at a density of about 20 million cells per plate. They were allowed to attach to the membrane filter overnight in buffer (RPMI from Life Technologies, Grand Island, N.Y.) containing 10 mM Hepes (Sigma, St Louis, Mo.) at pH 7.2 and 37° C. After the cells were attached to the filter, the media was removed, and the cells were washed with fresh buffer to remove any unattached cells. The filters were inverted cell-side down and placed at an angle to allow excess media to drain, and then dried for 20 minutes. This was timed so that the cell matrix could be immediately used in the assay described below.

Ligand Matrix

The ligand matrix was prepared by soaking $^{125}$I labeled IL-8 (Amersham, Inc., Arlington Heights, Ill.) into an agarose gel made by mixing 0.1 g agarose with 10 ml buffer, heating until molten, and then casting in a 8×7×0.075 cm gel apparatus. The gels were soaked overnight at RT while slowly mixing on a rotating platform (New Brunswick Scientific Co., Inc, Edison, N.J.). After soaking, the gels were dried for 20 minutes at RT just prior to use. This was timed so that the gel could be immediately used in the assay.

Sample Matrix

In the absence of a known inhibitor of the IL-8/cell receptor binding, nonradiolabeled IL-8 (Genzyme Corp., Cambridge, Mass.) was used as a control sample inhibitor to observe the inhibition of $^{125}$I-IL-8 binding to HEK cells. One microliter of 0, 0.03, 0.1, 0.3, 1, 3, 10, and 100 μM IL-8 was dispensed on a plastic sheet such as PVDC and dried for 1 hr under vacuum at RT.

Incubation

The sample matrix was placed on one side of the ligand matrix so that the dried IL-8 spots came into contact with the gel surface. The gel was inverted to allow the other side to dry for 10 minutes at RT and to allow the "inhibitor" to diffuse into the gel. Subsequently, the gels were placed on the non-cell side of the cell matrix. The binding reaction was allowed to incubate for 45 minutes at RT. Thereafter, the gels were removed, and the noncell side of the membrane was washed 4 times with buffer. The membranes were allowed to dry completely before they were removed from their plastic support ring. Then the membranes were imaged either with X-ray film or a phosphor imager (Molecular Dynamics, Sunnyvale, Calif.).

Figure 12:
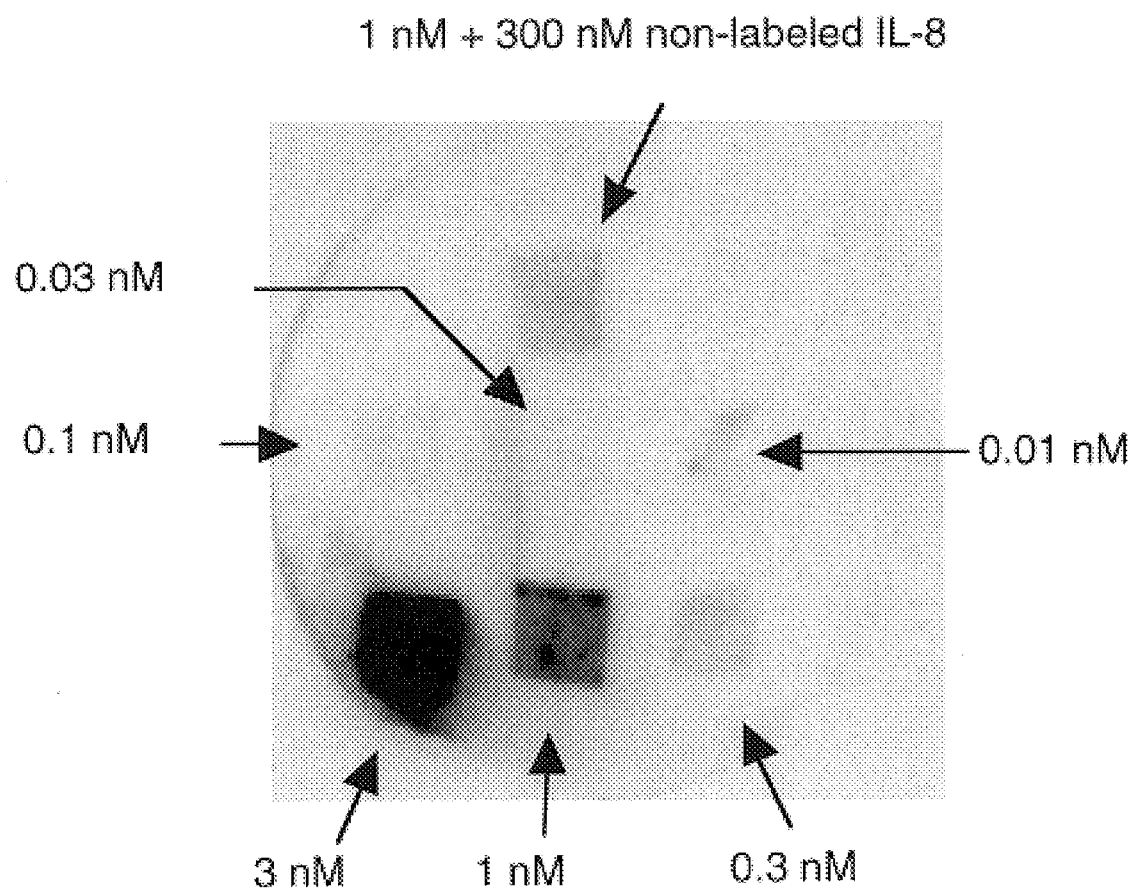
FIG. 12 illustrates a control experiment for ligand-cell interaction of radiolabeled IL-8.

FIG. 12 shows a dose response for $^{125}$I-IL-8 in agarose gels diffusing through a cell matrix to bind HEK cells expressing the IL-8a receptor. Several one cm$^2$ agarose squares were soaked in solutions of various $^{125}$I-IL-8 concentration as indicated. Subsequently, the ligand soaked squares were brought into contact with the cell matrix as described above. After incubation, the squares were removed from the cell matrix, and the non-cell side of the membrane was washed with buffer. A phosphor imager was used to locate the cell bound $^{125}$I-IL-8. The data indicate that a direct radiometric read-out in this gel-based cell assay is quantitatively dependent on the extent of ligand-receptor interaction. FIG. 12 also indicates that the binding areas remain distinct in shape, and confirms that lateral diffusion of signal is not a problem in the assay.

Figure 13:
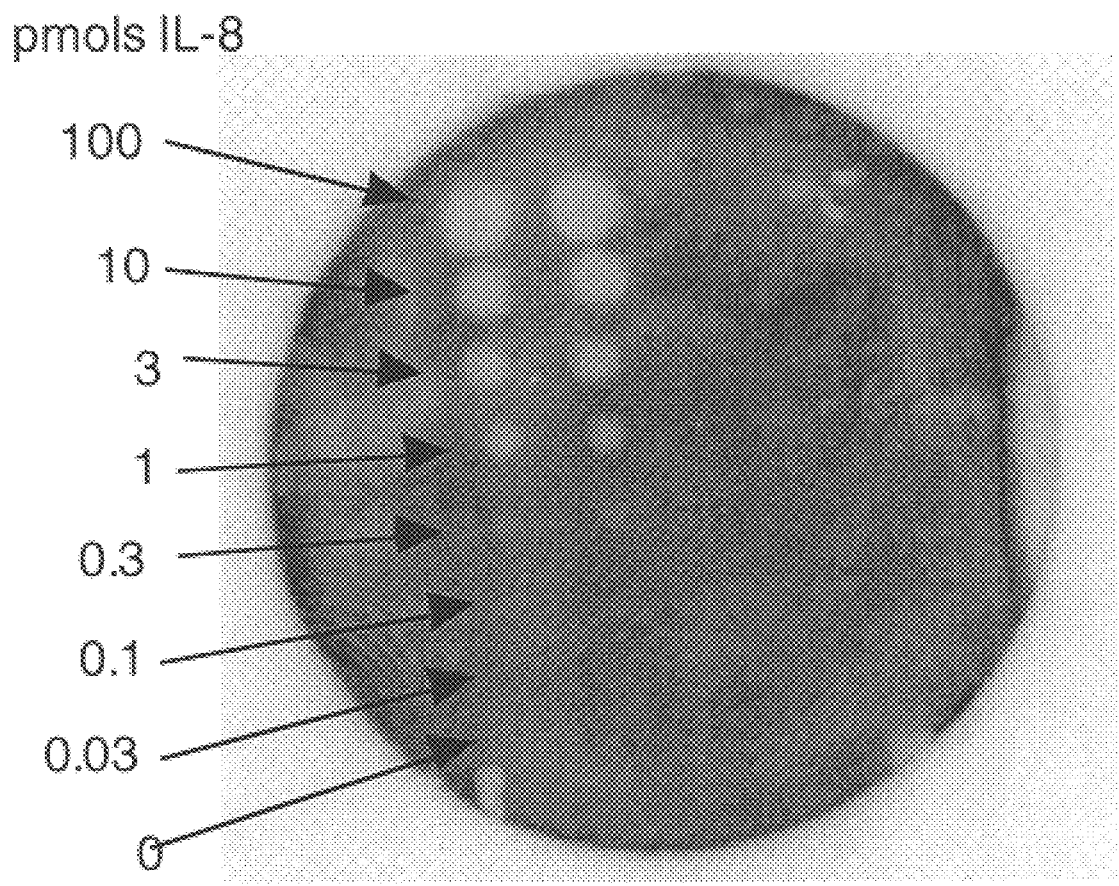
FIG. 13 illustrates the "inhibition" of IL-8 ligand-cell interaction.

FIG. 13 illustrates the results of the competitive inhibition experiment. Inhibition of binding between $^{125}$I-IL-8 and the HEK cells is indicted by the light spots. It is also readily apparent that inhibition by non-labeled IL-8 is quantifiably dose-dependent. Those data indicate that inhibitors, exemplified by non-labeled IL-8 in this case, can traverse the cell matrix to reduce binding between $^{125}$I-IL-8 and the cells.

Example 7
Filter-based, Gel-Less Functional Cell Assay

Changes in cellular function are often measured by observing the effect of test compounds or samples on reporter systems engineered into cells. Examples include looking at the effect on the synthesis of fluorescent intracellular proteins such as green fluorescent protein (GFP), extracellular proteins such as a receptor or adhesion molecule, or specific enzymes such as luciferase, chloramphenicol acetyltransferase, or β-galactosidase (Promega). First, the test compounds are incubated with the cells. Thereafter, the cells are allowed to express the reporter protein for a suitable period of time (could be minutes, hours or days). Then the level of the reporter protein is assayed by direct methods (e.g., GFP) or by indirect methods (e.g., ELISA techniques with membrane bound proteins). Further in the case of enzymes, the cell can be disrupted to extract the reporter protein and assay for the enzyme activity. Other functional cell assays measure the behaviour or localization of specific molecules such as dyes or radiolabeled metabolites in response to stimulation of a receptor or changes in cell physiology such as membrane potential.

An ELISA assay measuring the effect of compounds on the expression of Intercellular Adhesion Molecule-1 (ICAM-1) can be formatted for CF-HTS as follows. Endothelial cells expressing ICAM-1 are plated on a polycarbonate chemotaxis membrane (Neuro Probe) at about 5,000 cells/mm$^2$. The cells are incubated overnight at 37° C. in media. Medium is removed and the membranes are allowed to partially dry for 10 minutes at RT. Samples or compounds which are being tested for the induction of ICAM-1 are dried onto plastic sheets and placed in contact with the non-cell side of the moist membrane. The compounds are allowed to interact with the cells for 1 hr at 37° C. in a moist chamber, and thereafter the cells are bathed in media and incubated for 5 hrs at 37° C.

After allowing time for the cell to synthesize the induced protein, the media is removed from the membrane and the cells are incubated in buffer containing anti-ICAM-1 antibody (Genzyme, R&D systems) either unconjugated or conjugate with fluorescein isothiocyanate (FITC) or biotin. After a 30 minute incubation at RT, the buffer is removed and the cells are washed several times to remove unbound anti-ICAM-1. In the case of FITC conjugated antibody, the membrane is imaged using a CCD camera (Stratagene, Imaging Research) with 485 nm excitation and 520 nm emission. Compounds that stimulated ICAM-1 expression will result in a zone with increased fluorescence due to the binding of the FITC-anti-ICAM-1 antibody. In the case of biotin conjugated antibody, the cells are incubated in buffer containing avidin-HRP for 10 minutes at RT. The buffer is removed and the unbound avidin-HRP is washed away. The membranes are then bathed in buffer containing a precipitating HRP substrate such as diaminobenzidine tetrachloride (Pierce) and observed for color development in areas where the underlying cells were induced to express ICAM-1. In the case of the unconjugated anti-ICAM-1 antibody, a conjugated secondary anti-anti-ICAM-1 antibody is reacted with the cells followed by development of the signal with the appropriate substrate for the conjugate. Images are captured by a CCD camera. All of these variations (FITC, avidin-HRP, and anti-antiICAM-1) are alternative reporters that should give the same qualitative results—namely, samples that affect ICAM-1 expression can be correlated to zones of increased or decreased signal.

Note that the continuous-format matrices in this case are a membrane and a plastic sheet. A gel is not necessary for CF-HTS.

Example 8
CF-HTS Assay of Discrete Compounds for Neuraminidase Inhibition
Sample Matrix A library of 528 discrete, structurally related compounds were tested by CF-HTS. A Packard Multiprobe MP204 DT was used to dilute the compounds from vials into 96-well plates and to dilute and transfer the compounds onto plastic sheets. The compounds were initially diluted from 40 mM in DMSO in vials to 4 mM in DMSO in 96 well plates. Then they were diluted from 4 mM in DMSO to 200 μM in 50% EtOH/H$_2$O in 96 well plates. These samples were transferred in 1 ul duplicates onto 8 cm×8 cm plastic sheets with a spacing averaging 5 mm between samples (Bio-Rad cat. #165-2956) for a total of 192 samples per sheet. Each 1 ul spot, therefore, contained approximately 200 pmol of a particular compound from the library. As a control, a dilution series of 2,3-dehydro-2-deoxy-N-acetylneuraminic acid (DANA), a known neuraminidase inhibitor (Boehringer Mannheim #528544) was manually dispensed next to the compounds on each sheet. The sheets were dried in a vacuum oven so that each compound would be dried in its own location onto the plastic.

Enzyme Matrix

Before the assay, influenza neuraminidase enzyme was diluted 1500 fold from 25% glycerol, phosphate buffered saline into liquefied agar gel consisting of 1% Agarose, 50 mM sodium citrate pH 6.0, 10 mM calcium chloride at 40° C. A 8 cm×8 cm×0.75 mm enzyme gel was poured and solidified by reducing temperature to 4° C.

Substrate Matrix

A synthetic influenza neuraminidase substrate, 2'-(4methylumbeliferyl)-alpha-D-N-acetylneuraminic acid (Sigma cat.#M-8639), was diluted from 3 mM in DMSO to 30 μM into liquified agar gel and poured in a manner similar to the enzyme gel described above.

Incubation and Detection

The enzyme matrix was placed on the sample matrix on the side where the compounds of interest were dried. Then the substrate matrix was stacked on top of the enzyme matrix. The matrices were incubated at RT for 30 minutes. During this time, the quenched-fluorescent substrate and the enzyme diffused together between the two gels and the substrate was cleaved by the enzyme to produce an increase in fluorescence intensity. This was monitored by excitation at 340 nm and emission at 450 nm. Compounds that are capable of inhibiting enzyme activity minimized the increase in fluorescence intensity. As the gels increased in fluorescence intensity in most locations, the areas that contained enzyme inhibitors that were diffused into the gel from the plastic sheet were visible as darker areas having lower fluorescence. This was easily monitored by a CCD camera with proper filters to control emission and excitation wavelengths. The identity of compounds showing inhibitory zones was determined by the location of the zone with respect to the inhibitor matrix. By comparing the fluorescence of the DANA control with the known quantities of each inhibitor tested, a quantitative estimate of $IC_{50}$ was made for each compound.

Figure 14:
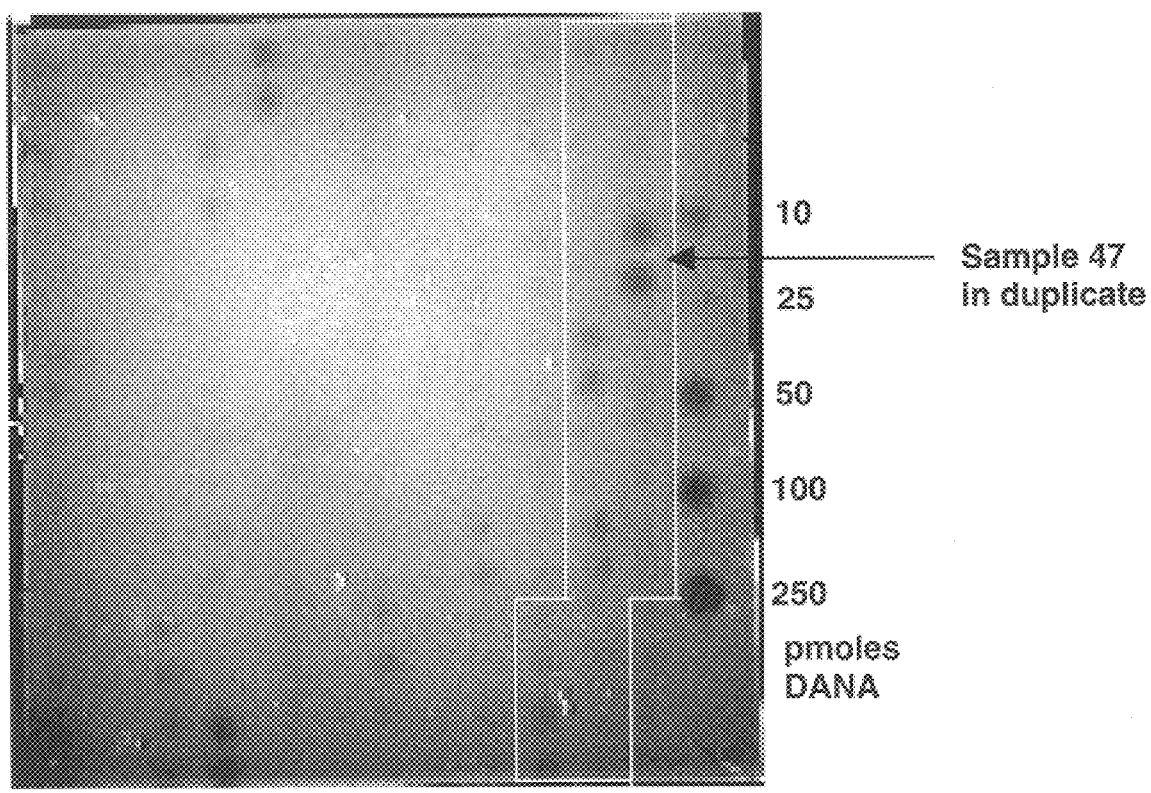
FIG. 14 illustrates an assay for inhibitors of neuraminidase.

All 528 compounds of a library were tested in duplicate. The total enzyme gel volume used was 33 ml, or 31.25 ul per test. Further, all compounds were tested simultaneously, and the assay conditions were constant as compared to the traditional 96-well assay. Furthermore as illustrated by FIG. 14, the assay was sensitive enough to detect inhibitors as weak as 100 μM. The estimated $IC_{50}$ values for active compounds agreed well with those observed for the same compounds tested by the more costly 96-well assay which required 200 ul per test. See Quantitative Gel Assay Results Table. This examples demonstrates that testing higher density arrays of compounds reduces cost and time. For example, even a minor reduction in spacing at 2.5 mm instead of 5 mm results in a four-fold increase in number of compounds tested per unit volume. In this experiment, this would have brought the volume per compound tested down below 10 ul. Yet the reagents are handled in bulk form, without the need for the low volume liquid handling equipment commonly used in miniaturized screening.

| | Quantitative Gel Assay Results | |
|---|---|---|
| Sample # | Approximate max Ki (μM) from Gel | Est. IC50s (μM) from 96-well assay |
| 34 | 100 | >100 |
| 35 | 80 | >100 |
| 36 | 80 | 42 |
| 37 | 100 | >100 |
| 38 | 100 | >100 |
| 39 | 100 | >100 |
| 40 | 40 | 32 |
| 41 | 100 | >100 |
| 42 | 40 | 50 |
| 43 | 100 | >100 |
| 44 | >200 | >100 |
| 45 | 100 | >100 |
| 46 | 100 | >100 |
| 47 | 10 | 7.5 |
| 48 | 100 | >100 |
| 49 | 100 | >100 |
| 50 | 100 | >100 |

Figure 15:
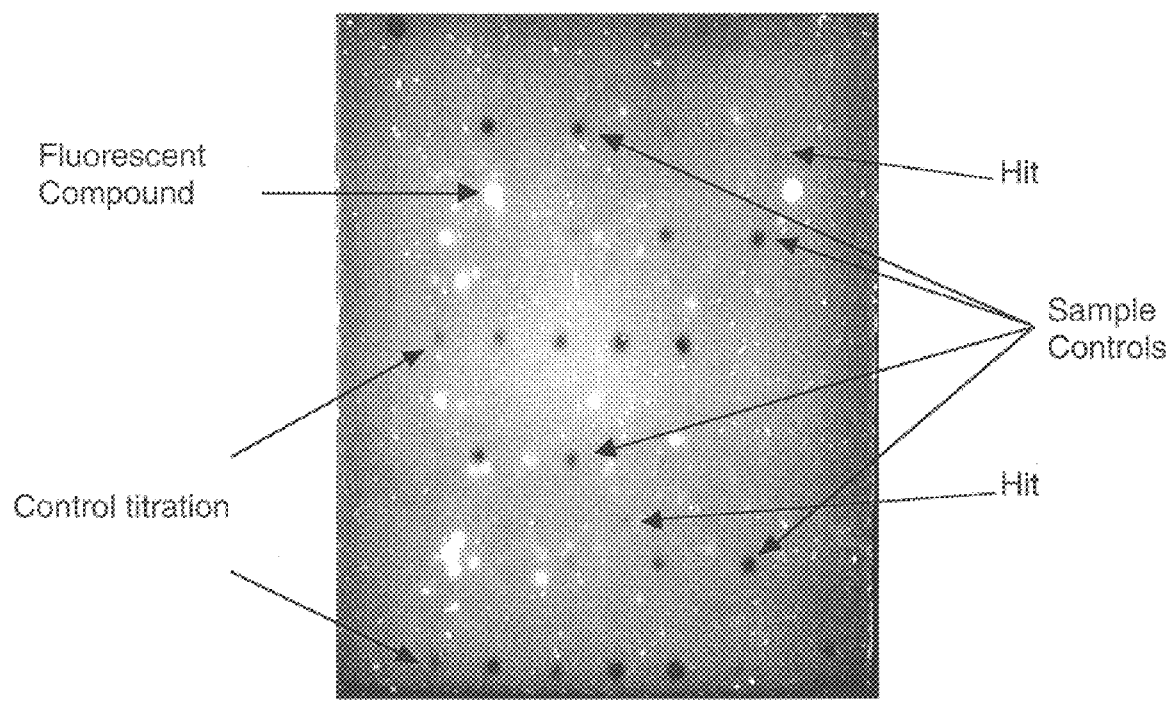
FIG. 15 illustrates a simultaneous assay of 10,080 discrete compounds for neuraminidase inhibition.

As a follow-up example to demonstrate the benefits of this miniaturization, 10,080 discrete compounds were tested by CF-HTS in a total enzyme gel volume of 17 ml (less than 2 ul per test). A Packard Multipette was used to dispense 30 nl volume of each sample separated by 1 mm. The compounds were dispensed in DMSO at a concentration of 5 mM, so that approximately 150 pmol of each was dispensed onto the plastic. DANA was again used as a control inhibitor. In addition to the usual control titration outside of the compound array, a control titration was included inside the array itself as a blind test in which the control samples were treated the same as the 10,080 unknowns when they were dispensed onto the plastic. As before, the sheets were dried and used in a neuraminidase assay. All 10,080 were simultaneously screened in less than one hour by this method. Once again, microfluidics and/or low volume handling were not required except when dispensing the initial compounds onto the sheet. The extremely high density used in this assay did not interfere with the detection of inhibitors. Furthermore, the high density did not complicate identification of active compounds even when fluorescent compounds (easily observed as brighter spots in the gel) were the nearest neighbors of active compounds. See FIG. 15.

We claim:

1. A process to simultaneously test a multitude of samples of different substances for their ability to enhance or inhibit a biological process comprising, a) depositing in an array a small volume of each of more than 96 samples of distinct substances onto a planar porous matrix containing or carrying a uniformly dispersed assay reagent such that each distinct substance is centered at its own distinct site and the identity of each substance can be determined from its deposition site, and b) observing the interaction of each substance with said assay reagent and correlating it to said substance's ability to enhance or inhibit said biological process.

2. A process to simultaneously test a multitude of samples of different substances for their ability to enhance or inhibit a biological process comprising, a) depositing in an array a small volume of each of more than 96 samples of distinct substances onto a planar matrix such that each distinct substance is centered at its own distinct site and the identity of each substance can be determined from its deposition site, b) bringing said matrix into contact with a porous matrix containing or carrying a uniformly dispersed assay reagent and allowing some of each substance to diffuse into said porous matrix in a manner that the spacial location of each diffused substance can be correlated to the site on said planar matrix at which said substance was originally deposited, and c) conducting an assay to determine the ability of each diffused substance to enhance or inhibit said biological process.

3. A process to simultaneously test a multitude of samples of different substances for their ability to enhance or inhibit a biological process comprising, a) depositing in an array a small volume of each of more than 96 samples of distinct substances onto a planar matrix such that each distinct substance is centered at its own distinct site and the identity of each substance can be determined from its deposition site, b) bringing said planar matrix into contact with a first porous matrix containing or carrying a uniformly dispersed first assay reagent and allowing some of each substance to diffuse into said porous matrix in a manner that the spacial location of each diffused substance can be correlated to the site on said planar matrix at which said substance was originally deposited, c) bringing said first porous matrix into contact with a second matrix carrying or containing a second uniformly dispersed assay reagent and allowing the second assay reagent to diffuse into the first porous matrix or allowing each substance and the first reagent to diffuse into the second matrix, in the latter case assuring that the diffusion occurs in such a manner that the location of each substance in the second matrix can be correlated to the site on said planar matrix at which said substance was originally deposited, and d) evaluating the ability of each substance to enhance or inhibit said biological process.

4. A process to simultaneously test a multitude of samples of different substances for their ability to enhance or inhibit a biological process comprising, a) depositing in an array a small volume of each of more than 96 samples of distinct substances onto a first planar porous matrix containing or carrying a uniformly dispersed first assay reagent such that each distinct substance is centered at its own distinct site and the identity of each substance can be determined from its deposition site, b) bringing said first porous matrix into contact with a second planar matrix carrying or containing a second uniformly dispersed assay reagent and allowing the second assay reagent to diffuse into the first porous matrix or allowing each substance and the first reagent to diffuse into or onto the second matrix, in the latter case assuring that the diffusion occurs in such a manner that the location of each substance in or on the second matrix can be correlated to the site on said first porous matrix at which said substance was originally deposited, and c) evaluating the ability of each substance to enhance or inhibit said biological process.

5. The process of claim 1 or 2 or 3 or 4 wherein one of the uniformly dispersed assay reagents is a macromolecule.

6. The process of claim 1 or 2 or 3 or 4 wherein one of the uniformly dispersed assay reagents is an enzyme.

7. The process of claim 1 or 2 or 3 or 4 wherein one of the uniformly dispersed assay reagents is a crude biological extract.

8. The process of claim 1 or 2 or 3 or 4 wherein one of the uniformly dispersed. assay reagents are organelles.

9. The process of claim 1 or 2 or 3 or 4 wherein one of the uniformly dispersed assay reagents are whole cells.

10. The process of claim 1 or 2 or 3 or 4 wherein a uniformly dispersed assay reagent are whole cells carried on one surface of a planar porous matrix.

11. The process of claim 10 wherein said interaction is observed by contacting said porous matrix with a solution or liquid suspension of a a reagent or a porous matrix containing a reagent which in either case aids in the visualization of a protein whose expression in said whole cells is the biological process being evaluated.

12. The process of claim 4 wherein the first assay reagent is a labeled ligand and the second assay reagent is an immobilized receptor for said ligand.

13. The process of claim 12 wherein the second planar matrix is washed to remove any labeled ligand which diffused onto or into said second planar matrix but did not become bound to said immobilized receptor.

14. The process of claim 13 wherein said second planar matrix is contacted with a solution or liquid suspension of a reagent or a porous matrix containing a reagent which in either case aids in the visualization of labeled ligand not removed by the washing step.

* * * * *